US010799312B2

(12) United States Patent
Tyler, II et al.

(10) Patent No.: US 10,799,312 B2
(45) Date of Patent: Oct. 13, 2020

(54) MEDICAL DEVICE STABILIZING APPARATUS AND METHOD OF USE

(71) Applicant: Edwards Lifesciences Corporation, Irvine, CA (US)

(72) Inventors: Gregory Scott Tyler, II, Huntington Beach, CA (US); Arnold Cruz Tuason, Claremont, CA (US); David M. Taylor, Lake Forest, CA (US); Matthew T. Winston, Aliso Viejo, CA (US); Alexander J. Siegel, Costa Mesa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 122 days.

(21) Appl. No.: 15/905,257

(22) Filed: Feb. 26, 2018

(65) Prior Publication Data

US 2018/0311474 A1    Nov. 1, 2018

Related U.S. Application Data

(60) Provisional application No. 62/491,392, filed on Apr. 28, 2017.

(51) Int. Cl.
*A61M 25/02* (2006.01)
*A61B 50/20* (2016.01)
(Continued)

(52) U.S. Cl.
CPC .............. *A61B 50/20* (2016.02); *A61B 50/15* (2016.02); *A61B 50/30* (2016.02); *A61B 90/50* (2016.02); *A61B 90/57* (2016.02); *A61F 2/2427* (2013.01); *A61M 5/1415* (2013.01); *A61M 25/02* (2013.01); *A61B 46/23* (2016.02); *A61B 2090/508* (2016.02); *A61F 2/24* (2013.01);
(Continued)

(58) Field of Classification Search
CPC ......... A61B 46/23; A61B 50/20; A61B 90/57; A61M 2025/024; A61M 25/02; A61M 5/1415
See application file for complete search history.

(56) References Cited

U.S. PATENT DOCUMENTS 3,874,388 A    4/1975  King et al.
4,340,091 A    7/1982  Skelton et al.
(Continued)

FOREIGN PATENT DOCUMENTS

CN        1142351 A      2/1997
CN      203355093 U     12/2013
(Continued)

OTHER PUBLICATIONS

Al Zaibag et al., "Percutaneous Balloon Valvotomy in Tricuspid Stenosis", British Heart Journal, vol. 57, No. 1, Jan. 1987.
(Continued)

*Primary Examiner* — Christine H Matthews
(74) *Attorney, Agent, or Firm* — Thomas C. Richardson

(57) ABSTRACT

A stabilizing apparatus for a medical device includes a housing having an aperture to receive the medical device. An engagement member is disposed in the housing. A biasing element urges the engagement member against a surface of the medical device, when the medical device is placed in the housing.

14 Claims, 19 Drawing Sheets

(51) Int. Cl.
    *A61F 2/24*      (2006.01)
    *A61B 50/15*     (2016.01)
    *A61B 50/30*     (2016.01)
    *A61B 90/50*     (2016.01)
    *A61B 90/57*     (2016.01)
    *A61M 5/14*      (2006.01)
    *A61B 46/23*     (2016.01)

(52) U.S. Cl.
    CPC . *A61M 2025/024* (2013.01); *A61M 2025/028* (2013.01); *A61M 2209/084* (2013.01)

(56) References Cited

U.S. PATENT DOCUMENTS

| | | |
|---|---|---|
| 4,506,669 A | 3/1985 | Blake, III |
| 4,533,179 A | 8/1985 | Nichols et al. |
| 4,590,937 A | 5/1986 | Deniega |
| 4,693,248 A | 9/1987 | Failla |
| 4,803,983 A | 2/1989 | Siegel |
| 4,951,576 A | 8/1990 | Cobos et al. |
| 5,125,895 A | 6/1992 | Buchbinder et al. |
| 5,171,252 A | 12/1992 | Friedland |
| 5,195,962 A | 3/1993 | Martin et al. |
| 5,246,109 A | 9/1993 | Markle et al. |
| 5,292,326 A | 3/1994 | Green et al. |
| 5,314,411 A | 5/1994 | Bierman et al. |
| 5,327,905 A | 7/1994 | Avitall |
| 5,359,741 A | 11/1994 | Lang |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Allen et al. |
| 6,629,534 B1 | 10/2003 | St. Goar et al. |
| 6,719,767 B1 | 4/2004 | Kimblad |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,569,062 B1 | 8/2009 | Kuehn et al. |
| 7,682,369 B2 | 3/2010 | Seguin |
| 7,731,706 B2 | 6/2010 | Potter |
| 7,744,609 B2 | 6/2010 | Allen et al. |
| 7,748,389 B2 | 7/2010 | Salahieh et al. |
| 7,753,932 B2 | 7/2010 | Gingrich et al. |
| 7,758,596 B2 | 7/2010 | Oz et al. |
| 7,776,017 B2 | 8/2010 | Ponzi et al. |
| 7,780,723 B2 | 8/2010 | Taylor |
| 7,803,185 B2 | 9/2010 | Gabbay |
| 7,824,443 B2 | 11/2010 | Salahieh et al. |
| 7,981,123 B2 | 7/2011 | Seguin |
| 7,988,724 B2 | 8/2011 | Salahieh et al. |
| 8,052,750 B2 | 11/2011 | Tuval et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,133,239 B2 | 3/2012 | Oz et al. |
| 8,147,542 B2 | 4/2012 | Maisano et al. |
| 8,162,898 B1 | 4/2012 | Wright |
| 8,206,437 B2 | 6/2012 | Bonhoeffer et al. |
| 8,211,064 B2 | 7/2012 | Sloan |
| 8,216,301 B2 | 7/2012 | Bonhoeffer et al. |
| 8,277,420 B2 | 10/2012 | Bierman et al. |
| 8,303,653 B2 | 11/2012 | Bonhoeffer et al. |
| 8,313,525 B2 | 11/2012 | Tuval et al. |
| 8,348,995 B2 | 1/2013 | Tuval et al. |
| 8,348,996 B2 | 1/2013 | Tuval et al. |
| 8,414,643 B2 | 4/2013 | Tuval et al. |
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,608,705 B2 | 12/2013 | Peters et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,734,400 B2 | 5/2014 | Ciccone |
| 8,740,918 B2 | 6/2014 | Seguin |
| 8,771,347 B2 | 7/2014 | DeBoer et al. |
| 8,778,017 B2 | 7/2014 | Eliasen et al. |
| 8,827,960 B2 | 9/2014 | Haak |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,945,177 B2 | 2/2015 | Dell et al. |
| 9,034,032 B2 | 5/2015 | McLean et al. |

(56) References Cited

U.S. PATENT DOCUMENTS

| | | | |
|---|---|---|---|
| 9,198,757 B2 | 12/2015 | Schroeder et al. |
| 9,220,507 B1 | 12/2015 | Patel et al. |
| 9,259,317 B2 | 2/2016 | Wilson et al. |
| 9,278,193 B2 | 3/2016 | Haider et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,427,327 B2 | 8/2016 | Parrish |
| 9,439,763 B2 | 9/2016 | Geist et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0034365 A1 | 2/2004 | Lentz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0127981 A1 | 7/2004 | Randert et al. |
| 2004/0127982 A1 | 7/2004 | Machold et al. |
| 2004/0147943 A1 | 7/2004 | Kobayashi |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2004/0267089 A1 | 12/2004 | Otsuka et al. |
| 2005/0049618 A1 | 3/2005 | Masuda et al. |
| 2005/0137690 A1 | 6/2005 | Saiahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0058738 A1* | 3/2006 | Ponzi ............. A61M 25/02 604/180 |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0178700 A1 | 8/2006 | Quinn |
| 2006/0224169 A1 | 10/2006 | Weisenburgh et al. |
| 2007/0010600 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Eliasen et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149001 A1 | 6/2008 | Hodges et al. |
| 2008/0167713 A1 | 7/2008 | Bolling |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005663 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0216197 A1 | 8/2009 | Russo |
| 2009/0275902 A1 | 11/2009 | Heeps et al. |
| 2009/0287304 A1 | 11/2009 | Dahlgren et al. |
| 2010/0022823 A1 | 1/2010 | Goldfarb et al. |
| 2010/0057192 A1 | 3/2010 | Celermajer |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0249497 A1 | 9/2010 | Peine et al. |
| 2010/0324595 A1 | 12/2010 | Linder et al. |
| 2011/0082538 A1 | 4/2011 | Dahlgren et al. |
| 2011/0137410 A1 | 6/2011 | Hacohen |
| 2011/0152779 A1 | 6/2011 | Panotopoulos |
| 2011/0245855 A1 | 10/2011 | Matsuoka et al. |
| 2011/0257723 A1 | 10/2011 | McNarnara |
| 2011/0295281 A1 | 12/2011 | Mizumoto et al. |
| 2012/0016312 A1 | 1/2012 | Brown et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0271237 A1 | 10/2012 | Andino |
| 2012/0316505 A1 | 12/2012 | Wright |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0094903 A1 | 4/2014 | Miller et al. |

(56) References Cited

U.S. PATENT DOCUMENTS

| | | |
|---|---|---|
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0261099 A1 | 9/2014 | Lewis et al. |
| 2014/0277404 A1 | 9/2014 | Wilson et al. |
| 2014/0277411 A1 | 9/2014 | Bortlein et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0005733 A1 | 1/2015 | Le et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0366666 A1 | 12/2015 | Khairkhahan et al. |
| 2016/0008131 A1 | 1/2016 | Christianson et al. |
| 2016/0022970 A1 | 1/2016 | Forcucci et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0317290 A1 | 11/2016 | Chau et al. |
| 2016/0331523 A1 | 11/2016 | Chau et al. |
| 2016/0354082 A1 | 12/2016 | Oz et al. |
| 2016/0367332 A1 | 12/2016 | Shah et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100236 A1 | 4/2017 | Robertson et al. |
| 2017/0239048 A1 | 8/2017 | Goldfarb et al. |
| 2017/0252154 A1 | 9/2017 | Tubishevitz et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0126124 A1 | 5/2018 | Winston et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |

FOREIGN PATENT DOCUMENTS

| | | |
|---|---|---|
| CN | 204337479 U | 5/2015 |
| EP | 0098100 A2 | 1/1984 |
| FR | 2146050 A5 | 2/1973 |
| FR | 9711600 | 3/1997 |
| WO | 8706474 A1 | 11/1987 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |

OTHER PUBLICATIONS

Al-Khaja et al., "Eleven Years' Experience with Carpentier-Edwards Biological Valves in Relation to Survival and Complications", European Journal of Cardio-thoracic Surgery 3: pp. 305-311, 1989.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Andersen, et al., "Transluminal implantation of artificial heart valves. Description of a new expandable aortic valve and initial results with implantation by catheter technique in closed chest pigs." European Heart Journal (1992), 13, 704-708.

Andersen, H.R. "History of Percutaneous Aortic Valve Prosthesis," Herz No. 34. pp. 343-346. 2009.

(56) References Cited

OTHER PUBLICATIONS

Batista RJ et al., "Partial left ventriculectomy to treat end-stage heart disease", Ann Thorac Surg., vol. 64, Issue—3, pp. 634-638, Sep. 1997.

Beall AC Jr. et al., "Clinical experience with a dacron velour-covered teflon-disc mitral-valve prosthesis", Ann Thorac Surg., vol. 5, Issue 5, pp. 402-410, May 1968.

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, pp. 654-670, 1964.

Fucci et al., "Improved results with mitral valve repair using new surgical techniques", Eur J Cardiothorac Surg. 1995;Issue 9, vol. 11, pp. 621-626.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Kolata, Gina "Device that Opens Clogged Arteries Gets a Failing Grade in a New Study", The New York Times, http://www.nytimes.com/1991/01/03/health/device-that-opens-clogged-arteries-gets-a-faili . . . , pp. 1-2, wrriten Jan. 3, 199, web page access Jul. 29, 2009.

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue—3, pp. 240-245, Mar. 1998.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

Praz et al., "Compassionate use of the PASCAL transcatheter mitral valve repair system for patients with severe mitral regurgitation: a multicentre, prospective, observational, first-in-man study," Lancet vol. 390, pp. 773-780, 2017.

Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1956.

Rashkind et al., "Historical Aspects of Interventional Cardiology: Past, Present, and Future", Texas Heart Institute Journal, Interventional Cardiology, pp. 363-367.

Reul RM et al., "Mitral valve reconstruction for mitral insufficiency", Prog Cardiovasc Dis., vol. 39, Issue—6, May-Jun. 1997.

Rosch, M.D., Josef, "The Birth, Early Years and Future of Interventional Radiology," J Vasc Interv Radiol 2003; 14:841-853.

Ross, D.N, "Aortic Valve Surgery", Surgery of the Aortic Valves, Guy's Hospital, London, pp. 192-197.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology: 176. pp. 535-538, 1990.

Serruys et al., "Stenting of Coronary Arteries. Are we the Sorcerer's Apprentice?", European Heart Journal, 10, 774-782, pp. 37-45, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida et al., "Modifications of Gianturco Expandable Wire Stents", Technical Note, American Roentgen Ray Society, pp. 1185-1187, May 1988.

Umaña JP et al., Bow-tie' mitral valve repair: an adjuvant technique for ischemic mitral regurgitation, Ann Thorac Surg., vol. 66, Issue—6, pp. 1640-1646, Nov. 1998.

Urban, Philip MD, "Coronary Artery Stenting", Editions Medecine et Hygiene, Geneve, pp. 1-47, 1991.

Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.

Wheatley, David J., "Valve Prosthesis", Rob & Smith's Operative Surgery, pp. 415-424, 1986.

\* cited by examiner

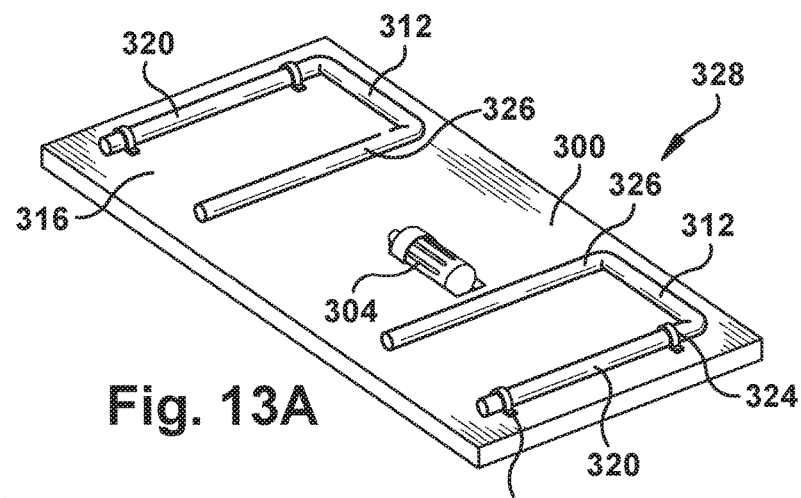
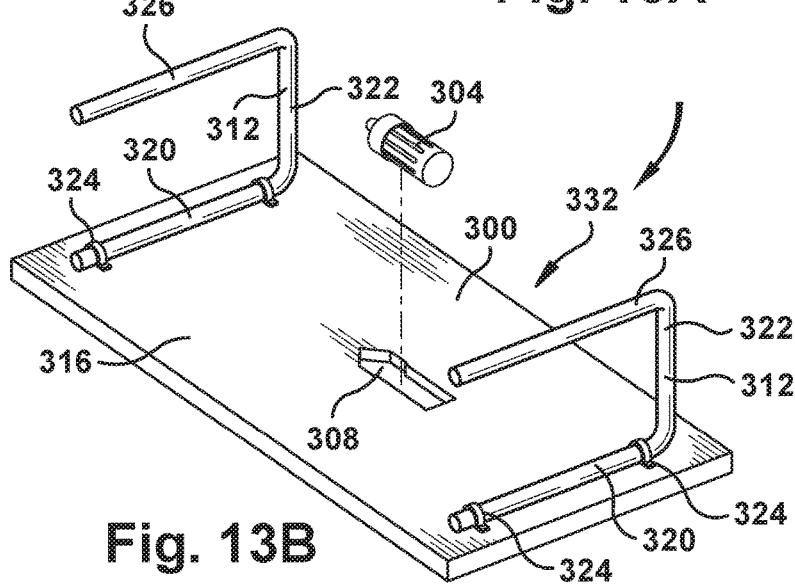
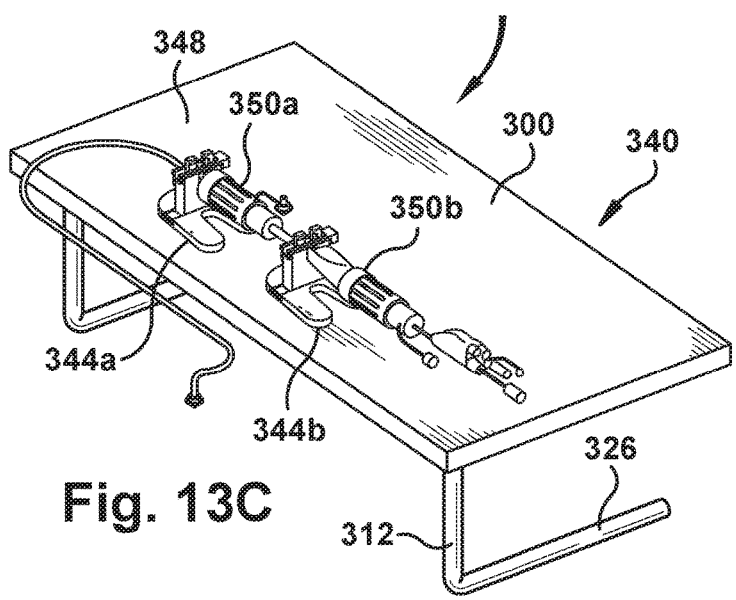

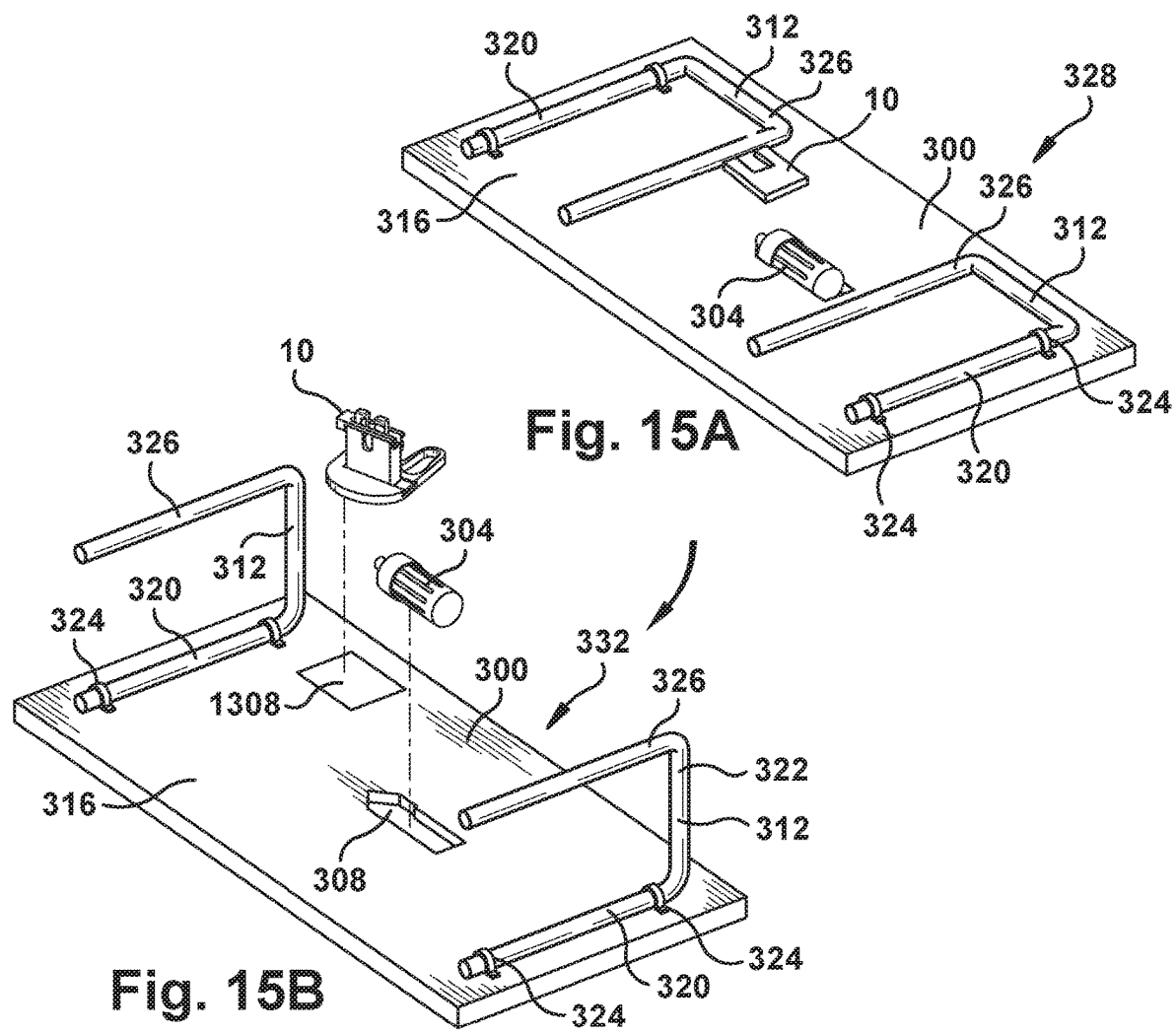
Fig. 15A
Fig. 15B
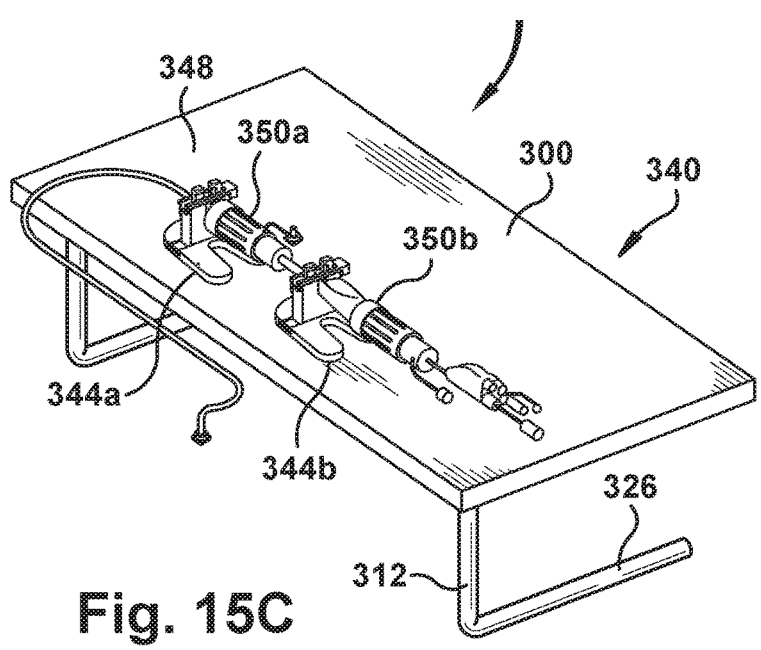
Fig. 15C

MEDICAL DEVICE STABILIZING APPARATUS AND METHOD OF USE

FIELD

The present disclosure relates generally to apparatuses useable to support or stabilize a medical device. Particular implementations relate to stabilizing devices having a passive locking mechanism and support tables useable therewith.

BACKGROUND

Prosthetic cardiac valves have been used for many years to treat cardiac valvular disorders. The native heart valves (such as the aortic, pulmonary, and mitral valves) serve critical functions in assuring the forward flow of an adequate supply of blood through the cardiovascular system. These heart valves can be rendered less effective by congenital, inflammatory, or infectious conditions. Such damage to the valves can result in serious cardiovascular compromise or death. For many years, the definitive treatment for such disorders was the surgical repair or replacement of the valve during open heart surgery, but such surgeries are prone to many complications. More recently, a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve, such as by inflating a balloon on which the prosthetic valve is mounted. Alternatively, the prosthetic valve can have a resilient, self-expanding stent or frame that expands the prosthetic valve to its functional size when it is advanced from a delivery sheath at the distal end of the catheter.

Balloon-expandable prosthetic valves typically are preferred for replacing calcified native valves because the catheter balloon can apply sufficient expanding force to anchor the frame of the prosthetic valve to the surrounding calcified tissue. On the other hand, self-expanding prosthetic valves sometimes are preferred for replacing a defective, non-stenotic (non-calcified) native valve, although they also can be used to replace stenotic valves.

In addition to valve replacement, transcatheter techniques can be used to repair heart valves. In some cases, repair devices, such as leaflet clips, can be used to improve coaptation of valve leaflets. In other cases, transcatheter techniques can be used to surgically alter a heart valve, such as surgically removing a portion of the native heart valve leaflets to reduce excessive slack.

Because the catheter must be directed through a patient's vasculature, it typically is beneficial for the operator to be able to precisely control the operation of the catheter, including mechanisms that allow the catheter to be bent to assist in navigating the vasculature, and mechanisms that control deployment of the prosthetic valve. During a procedure, the operator can control the catheter using a handle, which can provide controls for extending, retracting, and bending the catheter, including during navigating the patient's vasculature to the delivery or repair site.

Transcatheter procedures can have a long duration, and it may be inconvenient for an operator to manually maintain the position of the catheter handle during the entire procedure. While it may be desirable to adjust the location of the catheter handle relative to the patient at some points during the procedure, at other times it can be desirable to maintain the position of the catheter handle relative to the patient, such as to maintain the depth of insertion of the catheter or the rotational position of the handle.

A catheter handle be secured to a table proximate the patient using a locking mechanism. Typically, locking mechanisms require a user to actively engage or disengage a locking device to secure or release the catheter handle from a stand or mount. For example, a clamping mechanism may be advanced, such as by advancing a clamp over a threaded shaft, to secure the clamp against the catheter handle and thus secure the catheter handle during a procedure. If it is desired to adjust the position of the catheter handle, the clamp can be released, the position of the catheter handle and/or mount adjusted, and the clamp re-secured. However, these processes can be time consuming and inconvenient.

SUMMARY OF THE DISCLOSURE

An exemplary stabilizing apparatus for a medical device includes a housing having an aperture to receive the medical device. An engagement member is disposed in the housing. A biasing element urges the engagement member against a surface of the medical device, when the medical device is placed in the housing.

In certain exemplary embodiments, the aperture is positioned at an upper portion of the housing. In certain exemplary embodiments, the aperture is positioned at a lower portion of the housing. In certain exemplary embodiments, the aperture is positioned at a side portion of the housing.

In certain exemplary embodiments, the stabilizing apparatus further includes a door connected to the housing. The door has a first and second position. The door covers the aperture and passively engages the housing when the door is in the second position. In certain exemplary embodiments, the door is slideably adjustable from the first position to the second position. In certain exemplary embodiments, the door is pivotally adjustable from the first position to the second position.

In certain exemplary embodiments, the stabilizing apparatus passively clamps the medical device by releasing the engagement member. In certain exemplary embodiments, the biasing element is positioned below the medical device. In certain exemplary embodiments, the biasing element is positioned above the medical device. In certain exemplary embodiments, the biasing element is positioned to one side of the medical device. In certain exemplary embodiments, the housing is adjustable in height.

Various features as described elsewhere in this disclosure can be included in the examples summarized here and various methods and steps for using the examples and features can be used, including as described elsewhere herein. Any given embodiment of the present disclosure need not provide all features noted above, nor must it solve all problems or address all issues in the prior art noted above.

BRIEF DESCRIPTION OF THE DRAWINGS

Further understanding of the nature and advantages of the disclosed inventions can be obtained from the following description and claims, particularly when considered in conjunction with the accompanying drawings in which like parts bear like reference numerals.

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures may be drawn to scale for some embodiments, the figures are not necessarily drawn to scale for all embodiments. Embodiments of the present disclosure will be described and explained with additional specificity and detail through the use of the accompanying drawings.

FIGS. 13A-13C present perspective views illustrating a process for constructing a support table from medical device packaging.

FIG. 14B is a sectional view taken along the plane indicated by lines B-B of the exemplary shipping box 1400 of FIG. 14a.

FIGS. 15A-15C present perspective views illustrating a process for constructing a support table from medical device packaging.

DETAILED DESCRIPTION

The present disclosure provides examples of stabilizing units for a medical device. The stabilizing unit can comprise a passive locking mechanism, whereby the locking mechanism engages the medical device when not being actively disengaged by a physician. The present disclosure also provides support tables useable with one or more stabilizing units, including support tables constructible from medical device packaging.

Figure 1A:
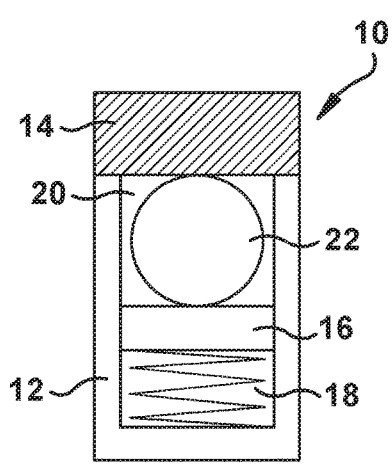
FIGS. 1A-1H are schematic views of exemplary embodiments of stabilizing apparatuses.

Referring first to FIG. 1A, there is shown an example stabilizing apparatus 10 comprising a housing 12 configured to receive a medical device 22. In certain embodiments, the medical device 22 is a catheter. A variety of different means for loading the medical device 22 into the housing are disclosed by the present application. For example, the housing 12 can have an aperture 20 and/or a door 14 to receive the medical device 22 (See FIGS. 1A-1H and 2A-2H. In certain embodiments, the optional door 14 retains a medical device 22 in a stabilizing apparatus 10. The optional door can be adjustable from a first position to a second position by sliding the door or pivoting the door. When the door is in the first or open position, the door 14 engages at least one surface of the housing 12. Additionally, the door 14 has a second position or a closed position as shown in FIG. 1. When the door is in a second position, the door 14 covers the aperture 20 and passively engages a second surface of the housing 12. In certain embodiments, the door 14 passively engages a second surface of the housing 12 using a passive clamping mechanism (i.e., a clamping mechanism that does not require the user to actively engage the clamp).

An engagement member 16 or engagement means engages at least one surface of the medical device. A variety of different engagement means are disclosed by the present application. For example, FIGS. 1A-1H, 2A-2I, 3A-3I, 4, 10, 11 and 12 illustrate different engagement means. The engagement member 16 and the housing 12 form a slot configured to receive the medical device 22. A biasing member 18 is coupled to the engagement member 16. The biasing member 18 urges the engagement member 16 against a surface of the medical device 22, when the medical device 22 is placed in the housing 12. A variety of different biasing means is disclosed in this application. For example, FIGS. 1A-1H and 2A-2H disclose a variety of different biasing means.

In FIG. 1A, the door 14 is positioned at an upper portion of the housing 12 and the engagement member 16 and the biasing member 18 are positioned at a lower portion of the housing 12. Thus, when the medical device 22 is placed in the housing 12, the biasing member 18 urges the engagement member 16 against a surface of the medical device 22 and the biasing member 18 urges an opposing surface of the medical device 22 against the door 14.

Figure 1B:
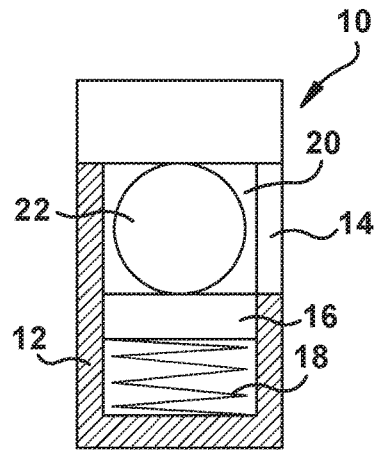

FIG. 1B illustrates another exemplary stabilizing apparatus 10 having the door 14 positioned at a side portion of the housing 12 and the engagement member 16 and the biasing member 18 are positioned at a lower portion of the housing 12. Thus, when the medical device 22 is placed in the housing 12, the biasing member 18 urges the engagement member 16 against a surface of the medical device 22 and the biasing member 18 urges an opposing surface of the medical device 22 against an upper portion of the stabilizing apparatus 10. The medical device is loaded into the housing 12 via the side door.

Figure 1C:
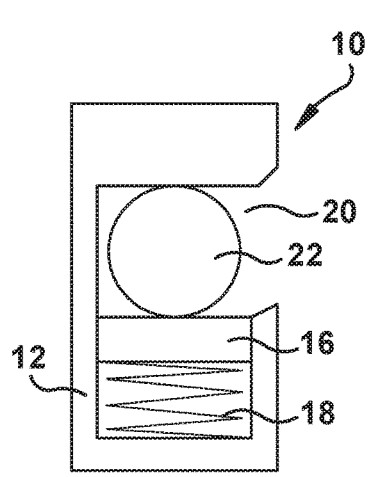

FIG. 1C illustrates another exemplary stabilizing apparatus 10 that is without the door. The engagement member 16 and the biasing member 18 are positioned at a lower portion of the housing 12. Thus, when the medical device 22 is placed in the housing 12, the biasing member 18 urges the engagement member 16 against a surface of the medical device 22 and the biasing member 18 urges an opposing surface of the medical device 22 against an upper portion of the stabilizing apparatus 10. The medical device is loaded into the housing 12 from the side of the housing 12.

Figure 1D:
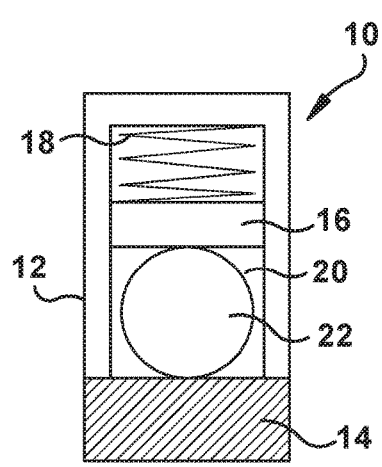

FIG. 1D illustrates another exemplary stabilizing apparatus 10 having the door 14 positioned at a lower portion of the housing 12 and the engagement member 16 and the biasing member 18 are positioned at an upper portion of the housing 12. Thus, when the medical device 22 is placed in the housing 12, the biasing member 18 urges the engagement member 16 against a surface of the medical device 22 and the biasing member 18 urges an opposing surface of the medical device 22 against the door 14. The medical device is loaded into the housing 12 via the bottom door 14.

Figure 1E:
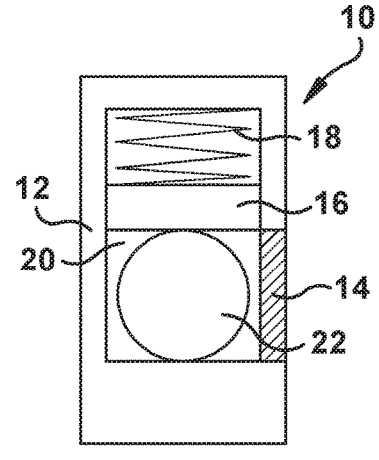

FIG. 1E illustrates another exemplary stabilizing apparatus 10 having the door 14 positioned at a side portion of the housing 12 and the engagement member 16 and the biasing member 18 are positioned at an upper portion of the housing 12. Thus, when the medical device 22 is placed in the housing 12, the biasing member 18 urges the engagement member 16 against a surface of the medical device 22 and the biasing member 18 urges an opposing surface of the medical device 22 against a lower portion of the stabilizing apparatus 10. The medical device is loaded into the housing 12 via the side door.

Figure 1F:
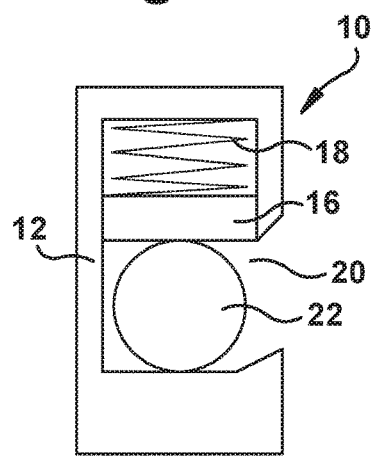

FIG. 1F illustrates another exemplary stabilizing apparatus 10 having no door. The engagement member 16 and the biasing member 18 are positioned at an upper portion of the housing 12. Thus, when the medical device 22 is placed in the housing 12, the biasing member 18 urges the engagement member 16 against a surface of the medical device 22 and the biasing member 18 urges an opposing surface of the medical device 22 against a lower portion of the housing 12. The medical device is loaded into the housing 12 from the side of the stabilizing apparatus 10.

Figure 1G:
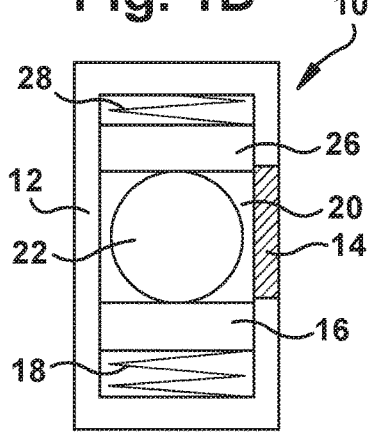

FIG. 1G illustrates another exemplary stabilizing apparatus having the door 14 positioned at a side portion of the housing 12. A first engagement member 16 and the first biasing member 18 are positioned at an upper portion of the housing 12. Additionally, a second engagement member 26 and a second biasing member 28 are positioned at a lower portion of the housing 12. Thus, when the medical device 22 is placed in the stabilizing apparatus 10, the first and second biasing members 18, 28 urge the first and second engagement members 16, 26 against opposing surfaces of the medical device 22. The medical device is loaded into the stabilizing apparatus 10 via the side door.

Figure 1H:
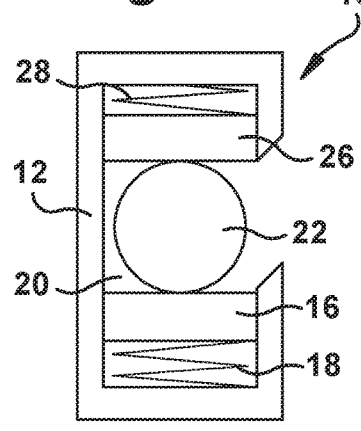

FIG. 1H illustrates another exemplary stabilizing apparatus 10 having no door. A first engagement member 16 and the first biasing member 18 are positioned at an upper portion of the stabilizing apparatus 10. Additionally, a second engagement member 26 and a second biasing member 28 are positioned at a lower portion of the stabilizing apparatus 10. Thus, when the medical device 22 is placed in the housing 12, the first and second biasing members 18, 28 urge the first and second engagement members 16, 26 against opposing surfaces of the medical device 22. The medical device is loaded into stabilizing apparatus 10 via an opening in the side of the apparatus.

In FIGS. 1A-1H, the biasing member is illustrated as a spring. However, the biasing member can be any variety of mechanisms, including without limitation, weights, magnets, hydraulic fluid, or pneumatic fluid.

Figure 2A:
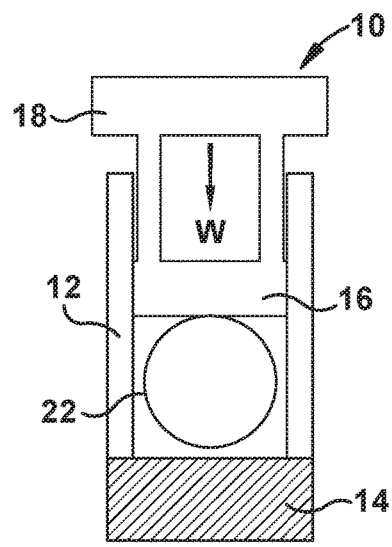
FIGS. 2A-2I are schematic views of other exemplary embodiments of stabilizing apparatuses.

FIG. 2A, illustrates an exemplary stabilizing apparatus 10 where the biasing member 18 comprises a weight. The door 14 is positioned at a lower portion of the stabilizing apparatus 10. The biasing member 18 is positioned at an upper portion of the stabilizing apparatus 10. In the illustrated embodiment, the stabilizing apparatus 10 further includes an engagement member 16, positioned at an upper portion of the stabilizing apparatus 10. However, the engagement member 16 is optional. When the medical device 22 is placed in the stabilizing apparatus 10, the biasing member 18 is urged against a surface of the medical device 22 and the biasing member 18 urges an opposing surface of the medical device 22 against the door 14.

Figure 2B:
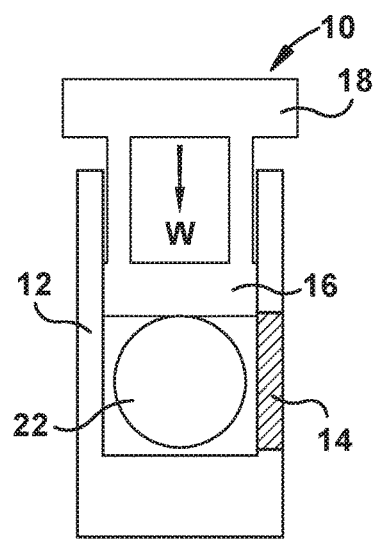

FIG. 2B, illustrates another exemplary stabilizing apparatus 10 where the biasing member 18 comprises a weight. The door 14 is positioned at a side portion of the stabilizing apparatus 10 and the biasing member 18 is positioned at an upper portion of the stabilizing apparatus 10. In the illustrated embodiment, the stabilizing apparatus 10 further includes an engagement member 16, positioned at an upper portion of the stabilizing apparatus 10. However, the engagement member 16 is optional. When the medical device 22 is placed in the stabilizing apparatus 10, the biasing member 18 is urged against a surface of the medical device 22 and the biasing member 18 urges an opposing surface of the medical device 22 against a lower portion of the stabilizing apparatus 10. The medical device is loaded into the stabilizing apparatus 10 via the side door.

Figure 2C:
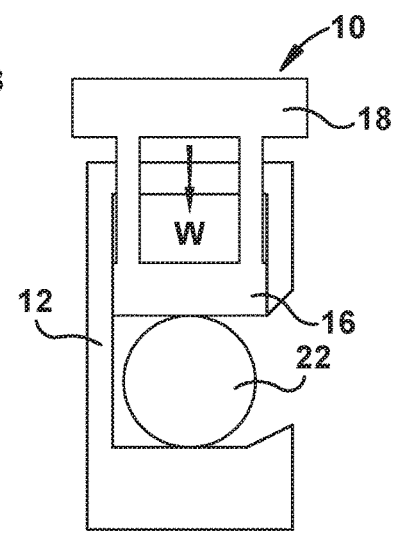

FIG. 2C, illustrates yet another exemplary stabilizing apparatus where the biasing member 18 comprises a weight. In the illustrated embodiment, there is no door and the biasing member 18 is positioned at an upper portion of the stabilizing apparatus 10. In the illustrated embodiment, the stabilizing apparatus 10 further includes an engagement member 16, positioned at an upper portion of the stabilizing apparatus 10. However, the engagement member 16 is optional. When the medical device 22 is placed in the stabilizing apparatus 10, the biasing member 18 is urged against a surface of the medical device 22 and the biasing member 18 urges an opposing surface of the medical device 22 against a lower portion of the stabilizing apparatus 10. The medical device is loaded into the stabilizing apparatus 10 from the side.

Figure 2D:
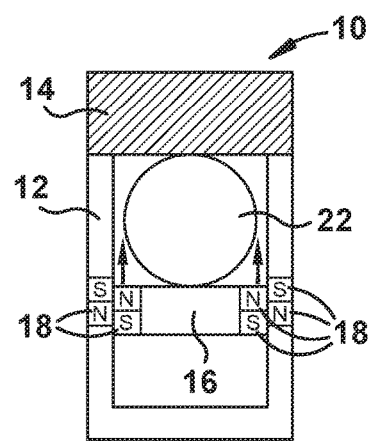

FIG. 2D, illustrates an exemplary stabilizing apparatus 10 where the biasing member 18 comprises magnets. The door 14 is positioned at an upper portion of the stabilizing apparatus 10 and the engagement member 16 and the biasing member 18 are positioned at a lower portion of the stabilizing apparatus 10. Thus, when the medical device 22 is placed in the stabilizing apparatus 10, the biasing member 18 urges the engagement member 16 against a surface of the medical device 22 and the biasing member 18 urges an opposing surface of the medical device 22 against the door 14.

Figure 2E:
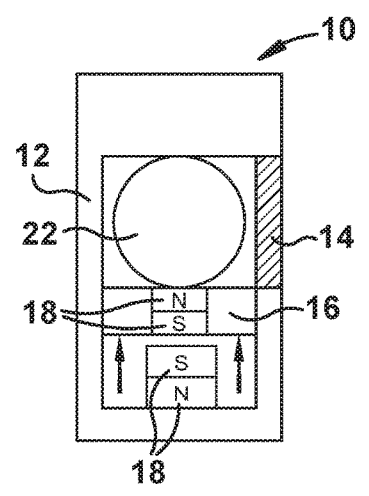

FIG. 2E, illustrates another exemplary stabilizing apparatus 10 where the biasing member 18 comprises magnets. The door 14 is positioned at a side portion of the stabilizing apparatus 10 and the engagement member 16 and the biasing member 18 are positioned at a lower portion of the stabilizing apparatus 10. Thus, when the medical device 22 is placed in the stabilizing apparatus 10, the biasing member 18 urges the engagement member 16 against a surface of the medical device 22 and the biasing member 18 urges an opposing surface of the medical device 22 against an upper portion of the stabilizing apparatus 10. The medical device is loaded into the stabilizing apparatus 10 via the side door.

Figure 2F:
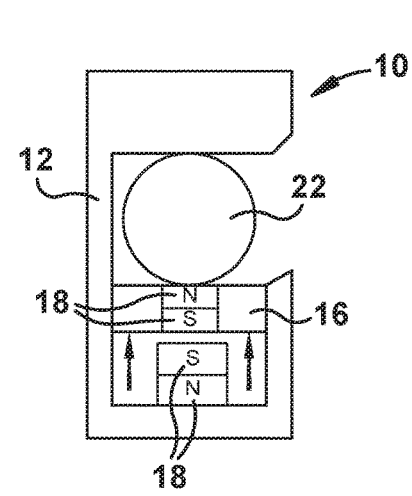

FIG. 2F, illustrates yet another exemplary stabilizing apparatus 10 where the biasing member 18 comprises magnets. In the illustrated embodiment, there is no door. The engagement member 16 and the biasing member 18 are positioned at a lower portion of the stabilizing apparatus 10. Thus, when the medical device 22 is placed in the stabilizing apparatus 10, the biasing member 18 urges the engagement member 16 against a surface of the medical device 22 and the biasing member 18 urges an opposing surface of the medical device 22 against an upper portion of the stabilizing apparatus 10. The medical device is loaded into the stabilizing apparatus 10 from the side of the stabilizing apparatus 10.

Figure 2G:
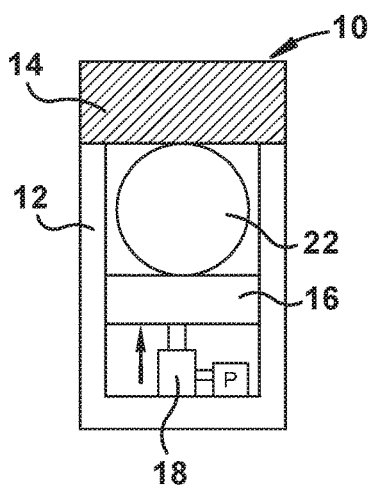

FIG. 2G, illustrates an exemplary stabilizing apparatus 10 where the biasing member 18 comprises a hydraulic or pneumatic cylinder. The door 14 is positioned at an upper portion of the stabilizing apparatus 10. The engagement member 16 and the biasing member 18 are positioned at a lower portion of the stabilizing apparatus 10. Thus, when the medical device 22 is placed in the stabilizing apparatus 10, the biasing member 18 urges the engagement member 16 against a surface of the medical device 22 and the biasing member 18 urges an opposing surface of the medical device 22 against the door 14.

Figure 2H:
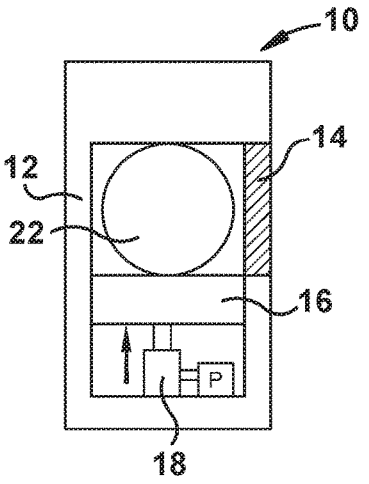

FIG. 2H, illustrates another exemplary stabilizing apparatus 10 where the biasing member 18 comprises a hydraulic or pneumatic cylinder. The door 14 is positioned at a side portion of the stabilizing apparatus 10. The engagement member 16 and the biasing member 18 are positioned at a lower portion of the stabilizing apparatus 10. Thus, when the medical device 22 is placed in the stabilizing apparatus 10, the biasing member 18 urges the engagement member 16 against a surface of the medical device 22 and the biasing member 18 urges an opposing surface of the medical device 22 against an upper portion of the stabilizing apparatus 10. The medical device is loaded into the stabilizing apparatus 10 via the side door.

Figure 2I:
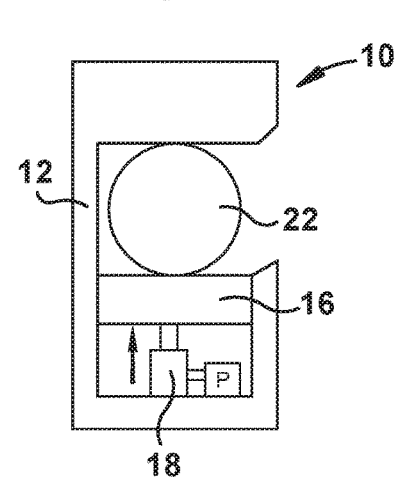

FIG. 2I, illustrates yet another exemplary stabilizing apparatus where the biasing member 18 comprises a hydraulic or pneumatic cylinder. There is no door and the engagement member 16 and the biasing member 18 are positioned at a lower portion of the stabilizing apparatus 10. Thus, when the medical device 22 is placed in the stabilizing apparatus 10, the biasing member 18 urges the engagement member 16 against a surface of the medical device 22 and the biasing member 18 urges an opposing surface of the medical device 22 against an upper portion of the stabilizing apparatus 10. The medical device is loaded into the stabilizing apparatus 10 from the side of the stabilizing apparatus 10.

The engagement member 16 can take a wide variety of different forms. For example, the engagement member can be flat as illustrated by FIG. 1A-1H or be contoured as illustrated by FIGS. 3A, 3C, 3D, 3F, 3G, 3H and 3I. In the embodiments illustrated by FIGS. 3A-3I, the engagement members 16 in these embodiments comprise at least one arm 32 and a base 34. The arm 32 allows the engagement member to be pressed down to quickly release the clamp. The biasing member 18 urges the engagement member 6 against a surface of the medical device 22, when the medical device 22 is placed in the stabilizing apparatus 10. In any of the stabilizing apparatuses illustrated in FIGS. 3A-3I, the biasing member may comprise a spring, weight, magnets, a hydraulic or pneumatic cylinder, or various other similar device such that the engagement member is biased toward the medical device as described below.

In the embodiments illustrated by FIGS. 3A-3B and 3D-3E, the stabilizing apparatus 10 further comprising a pin 36 inside the housing 12. The biasing member 18 urges the pin 36 against a surface feature of a medical device 22. When the medical device 22 is placed in the stabilizing apparatus 10, the pin 36 engages a surface feature in the medical device 22, such that the medical device 22 is prevented from lateral, rotational, and/or horizontal movement. In the embodiments illustrated by FIGS. 3A and 3D, the pin 36 is connected to the engagement member 16. In the embodiments illustrated by FIGS. 3B and 3E, the pin 36 is connected to the door 14. In the embodiments illustrated by FIGS. 3B and 3E, the pin 36 further comprises a roller ball 38 in a portion of the pin 36 that contacts the medical device, which allows the pin 36 to be moveable along the surface of the medical device. However, when the roller ball 38 engages a recessed surface feature in the medical device 22, the medical device 22 is prevented from lateral, rotational, and/or horizontal movement.

Figure 3A:
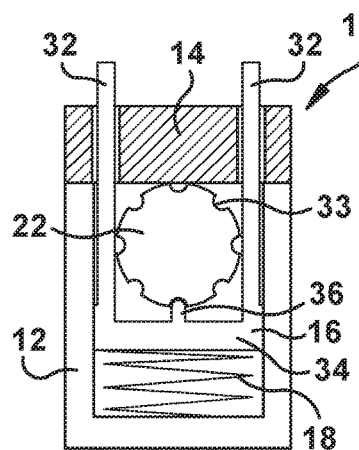
FIGS. 3A-3I are schematic views of exemplary embodiments of stabilizing apparatuses.
Figure 3B:
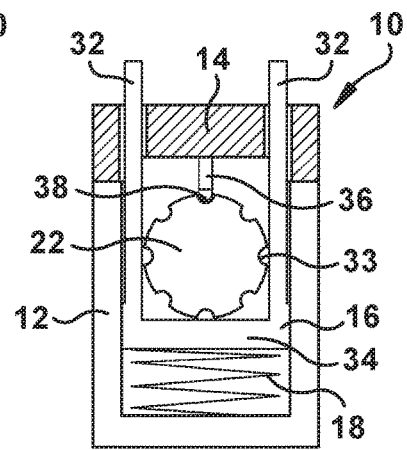
Figure 3C:
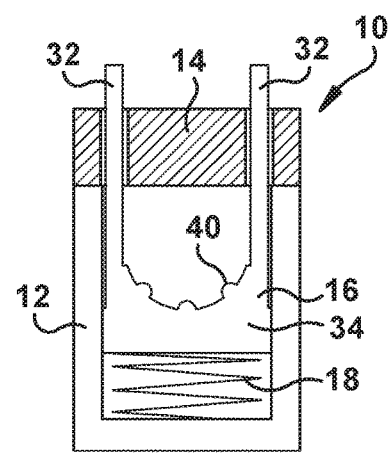
Figure 3D:
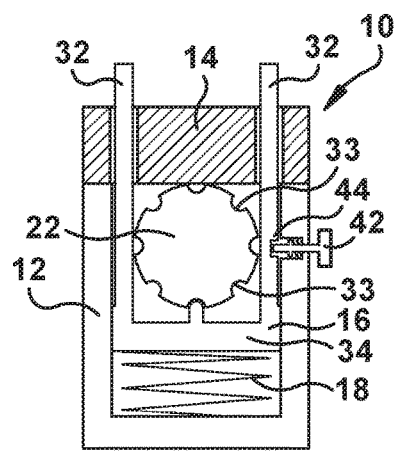
Figure 3E:
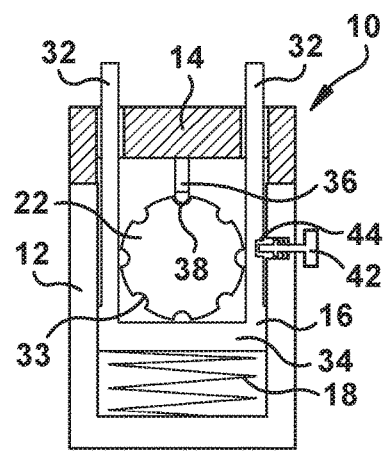
Figure 3F:
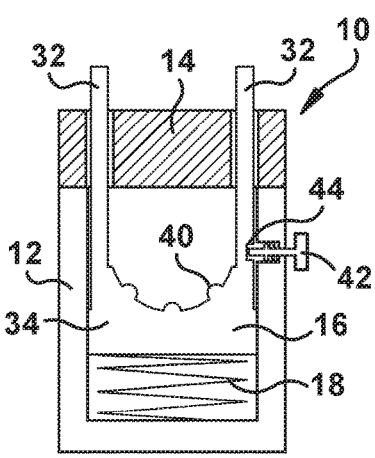

In the embodiments illustrated by FIGS. 3D-3F, the stabilizing apparatus 10 further comprises a lock 42 connecting the engagement member 16 and the housing 12. The lock 42 can take a wide variety of different forms. Any locking means or arrangement that locks the position of the engagement member 16 relative to the housing can be used. In the illustrated embodiment, the lock 42 is pulled against a biasing force of a spring to release the lock. The lock 42 passively locks the engagement member 16 in place by placing one end of the lock 42 into a slot 44 in the engagement member 16. When the biasing member 18 urges the engagement member 16 into the base 14, one end of the lock 42 is captured in the slot 44, thus preventing further motion of the engagement member 16. A user must manually or actively release the lock 42 to remove the end of the lock 42 from the slot.

In the embodiments illustrated by FIGS. 3C and 3F-3I, the engagement member 16 comprises at least one mating ridge 40 shaped to mate with at least one recess in the medical device (for example, the surface feature 33 in the medical device 22, shown in FIGS. 3A-3B and 3D-3E). When at least one surface feature 33 of the handle of the medical device engages with at least one mating ridge 40 of the engagement member 16, the mating of the ridge 40 and the surface feature 33 helps secure the handle of the medical device against lateral, rotational, and/or horizontal movement. In the embodiment illustrated by FIG. 3C, the mating ridges 40 are in the base 34. However, in certain embodiments, the mating ridges 40 may be in at least one arm 32 (not shown) or in another location.

Figure 3G:
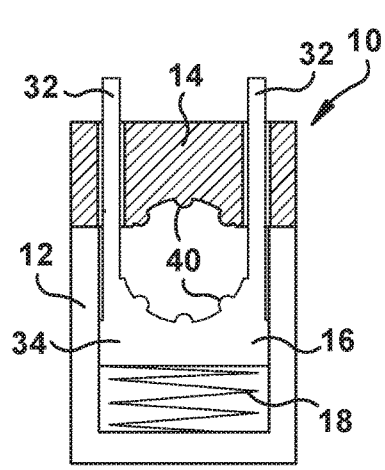

In the embodiment illustrated by FIG. 3G, the mating ridges 40 are in the base 34 and the door 14. The engagement member 16 comprises a base 34 and two arms 32. The clamping member and the biasing member 18 are positioned at a lower portion of the housing 12. The door is positioned at an upper portion of the housing. Thus, when the biasing member 18 urges the engagement member 16 toward the door 14 and the medical device 22 is placed in the housing 12, the biasing member 18 urges the engagement member 16 against a surface of the medical device 22 and the biasing member 18 urges an opposing surface of the medical device 22 against the door 14. The medical device is loaded into the housing 12 from an upper portion of the housing 12.

Figure 3H:
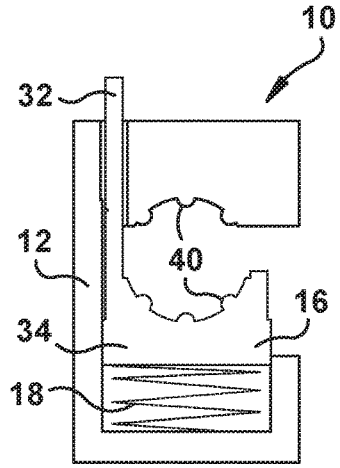

In the embodiment illustrated by FIG. 3H, there is no door. The engagement member 16 comprises a base 34 and one arm 32. The mating ridges 40 are in the base 34 and an upper portion of the housing 12. The engagement member 16 and the biasing member 18 are positioned at a lower portion of the housing 12. Thus, when the medical device 22 is placed in the housing 12, the biasing member 18 urges the engagement member 16 against a surface of the medical device 22 and the biasing member 18 urges an opposing surface of the medical device 22 against an upper portion of the housing 12. The medical device is loaded into the housing 12 from the side of the housing 12.

Figure 3I:
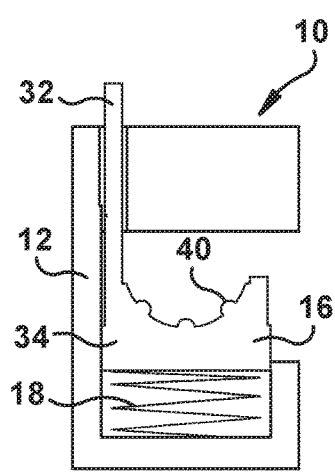

In the embodiment illustrated by FIG. 3I, there is no door. The engagement member 16 comprises a base 34 and one arm 32. The mating ridges 40 are located on the base 34. There are optionally no mating ridges in an upper portion of the housing 12. The engagement member 16 and the biasing member 18 are positioned at a lower portion of the housing 12. Thus, when the medical device 22 is placed in the housing 12, the biasing member 18 urges the engagement member 16 against a surface of the medical device 22 and the biasing member 18 urges an opposing surface of the medical device 22 against an upper portion of the housing 12. The medical device is loaded into the housing 12 from the side of the housing 12.

Figure 4:
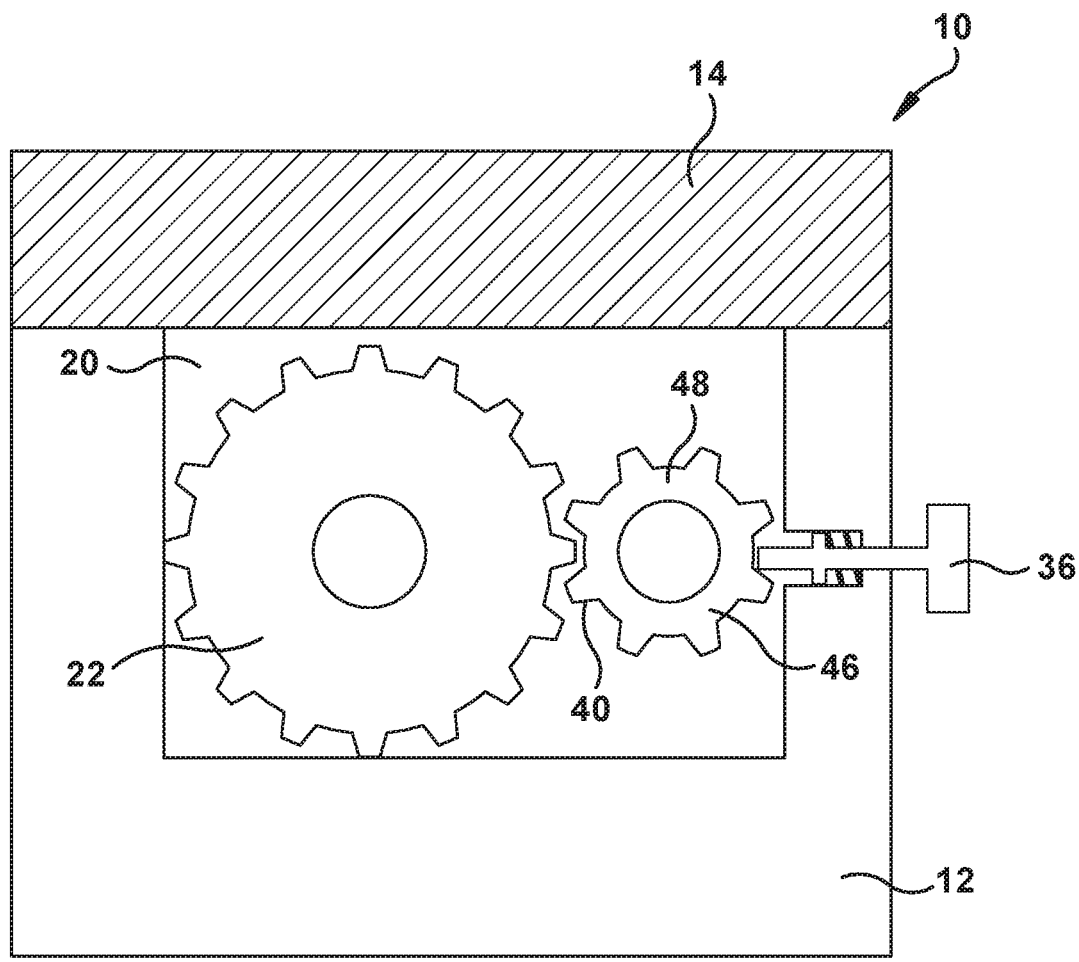
FIG. 4 is a schematic view of an exemplary embodiment of a stabilizing apparatus.

In the embodiment illustrated by FIG. 4, the stabilizing apparatus 10 comprises a selectively lockable gear 46. Any of the stabilizing apparatuses disclosed herein may include a selectively lockable gear 46. A housing 12 has an aperture 20 to receive the medical device 22. A door 14 is connected to the housing 12 and has a first position where the door 14 is open (not shown) and second position. The door 14 covers the aperture 20 and passively engages the housing 12 when the door 14 is in the second position. The selectively lockable gear 46 comprises a rotating portion 48 and a pin 36. In the illustrated embodiment, the rotating portion 48 is positioned inside the housing. However, in certain embodiments the rotating portion may be located outside the housing. The pin 36 passively contacts the rotating portion 48, thereby locking the rotating portion and preventing it from rotation. The rotating portion includes mating ridges 40 that are configured to mate with the medical device and thus prevent the medical device from rotating when engaged with the selectively lockable gear.

Figure 5:
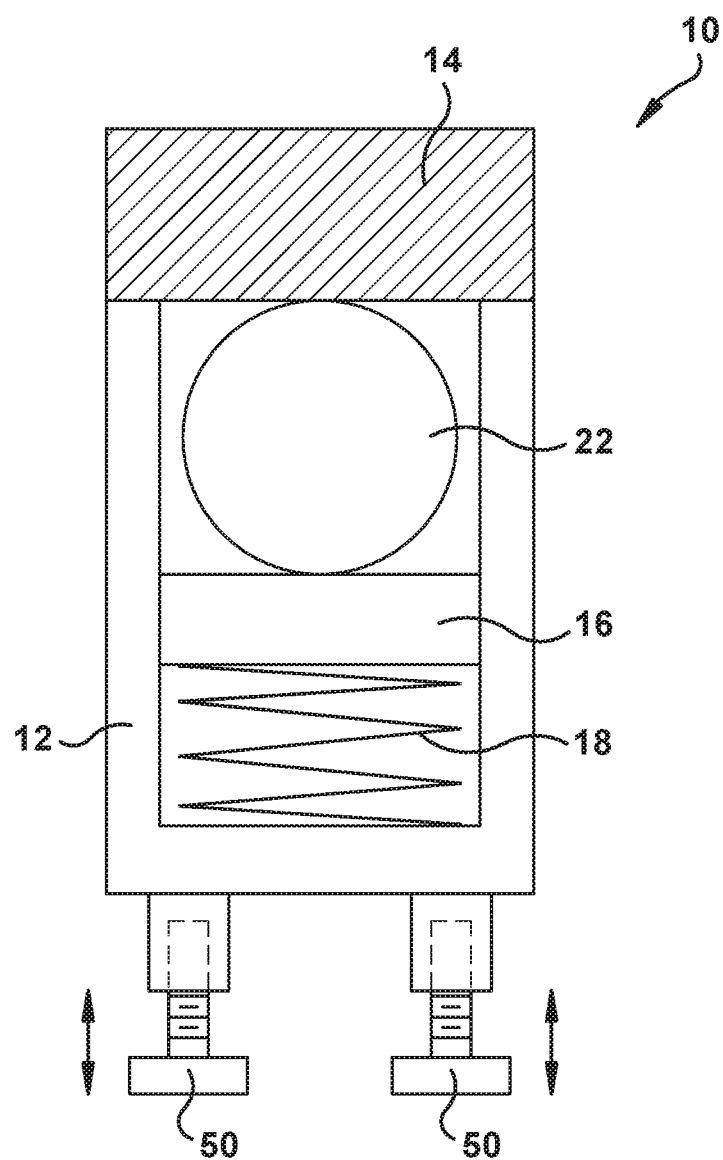
FIG. 5 is a schematic view of an exemplary embodiment of a stabilizing apparatus.

FIG. 5 illustrates a stabilizing apparatus with height adjustable legs. Any of the stabilizing apparatuses disclosed herein may include a height adjustment mechanism 50. In the illustrated embodiment, the height adjustment mechanism comprises a screw portion connected to a leg. The leg may be at least partially hollow and include a female threading configured to receive the male threading of the screw portion. However, the height adjustment mechanism may take a variety of different forms.

Figure 6:
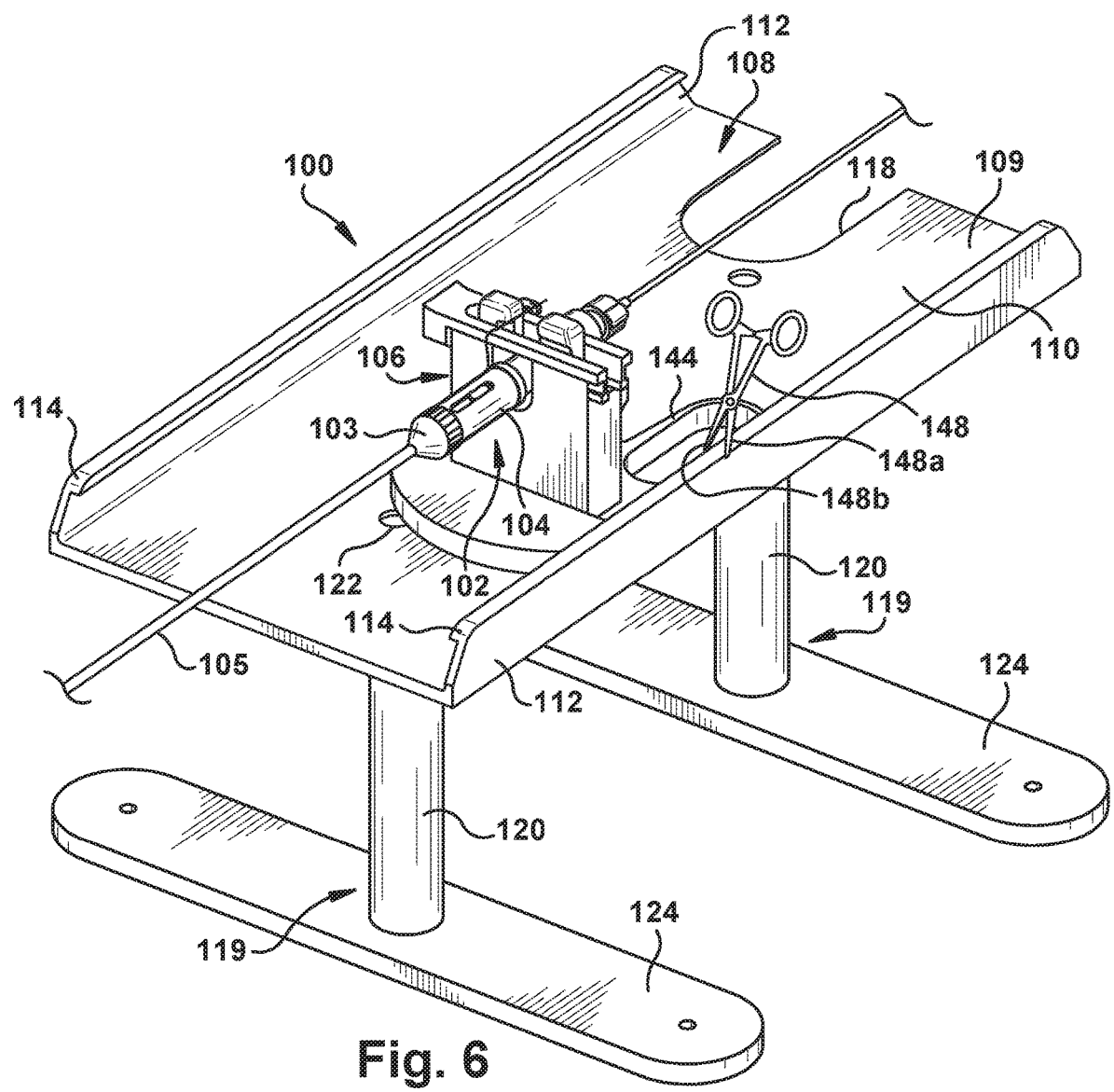
FIG. 6 is a perspective view of a support table and an example embodiment of a stabilizing apparatus useable with a medical device.

Referring to FIG. 6, there is shown an example of a stabilizing system 100 for a medical device 102, such as a transcatheter delivery system comprising a catheter 103 having a handle 104 coupled to an axially extending shaft 105, a distal end of which can be inserted into the vasculature of a patient. The stabilizing system 100 is shown with an example of a stabilizing unit 106 (also referred to herein as a stabilizing device or stabilizing apparatus) and a table or platform 108 on which the stabilizing unit can be placed or mounted. The handle 104 of the catheter 103 can be releasably mounted on the stabilizing unit 106.

The catheter 103 can be used for delivering any of various types of implantable medical devices into a patient's body, including, without limitation, prosthetic valves (e.g., prosthetic heart valves), stents, stent-grafts, and various types of leaflet or valve repair devices, such as annuloplasty devices, leaflet clips, and the like. In some implementations, the medical device 102 may comprise an assembly comprised of multiple catheters that are insertable into a patient's body. The handle of each catheter can be mounted on a separate stabilizing unit 106, with all stabilizing units 106 supported on the same platform, or on separate platforms.

The table 108 can comprise a generally horizontal portion 109 and a plurality of support members 119. The horizontal portion can define a generally planar mounting surface 110 onto which the stabilizing unit 106 can be placed or mounted. The table 108 can have vertical sides 112 extending upwardly from the longitudinal edges of the horizontal portion 109. The sides 112 can define laterally inwardly extending lips 114 that can define mounting ridges to which the stabilizing unit 106 can be secured, as further described below.

The table 108 can comprise a semi-circular cutout section 118 at a longitudinal end portion of the horizontal portion 109. The cutout section 118 can facilitate operator access to the stabilizing unit 106, including the handle 104 of the catheter 103 secured therein. In other cases, the cutout section 118 can have a different shape, can be located within another portion of the table 108, or can be omitted. Although the table 108 is shown with a rectangular mounting surface 110, the mounting surface can have other shapes, including square, triangular, round, or elliptical shapes.

The plurality of support members 119 can each comprise a vertical component or leg 120 and a horizontal component or foot 124. Each leg 120 can extend downwardly from (such as abutting), and orthogonally to, a lower surface of the horizontal portion 109. The horizontal portion 109 can comprise threaded mounting apertures 122 that receive axially-extending threaded upper end portions (not shown) of the legs 120. A foot 124 can extend laterally from a bottom axial end of each leg 120.

Each leg 120 can comprise an externally threaded lower end portion that threadably engages a mating threaded aperture of its respective foot 124. Alternatively, the feet 124 can comprise axially extending threaded posts that extend into internally threaded apertures in the bottom axial ends of the legs 120. In yet further implementations, the feet 124 and the legs 120 can be securely coupled in another manner, such as by welding or the use of a suitable adhesive, fasteners (e.g., screws), or the support members 119 can be of unitary construction (e.g., the legs 120 and feet 124 molded as a unit). The feet 124 can be dimensioned and shaped such that they can be placed on a surface, such as an operating table, to provide resistance against tipping or torsional movement of the table 108, thus maintaining the mounting surface 110 in an at least substantially horizontal position.

In particular examples, components of the table 108 can be dimensioned and positioned with respect to one another such that the table may be placed between the legs of a patient lying on an operating table. For example, the legs 120 can be placed between the patient's legs, with the feet 124 resting on an operating table. The patient's legs can be placed over the feet 124 to help maintain the table 108 in a desired position, including resisting translational and torsional movement. The feet 124 can have a width that is sufficiently small such that placing the legs of the patient over the feet does not cause the patient discomfort. The feet 124 can have a length sufficiently long to extend underneath the legs of a patient such that the patient's legs can rest on top of the feet and help secure the table 108 in place relative to the patient during a procedure. If desired, the table 108 can be further anchored in place against the patient and/or the operating table, such as by using fasteners, adhesive tape, sutures, or other fastening means.

Figure 10:
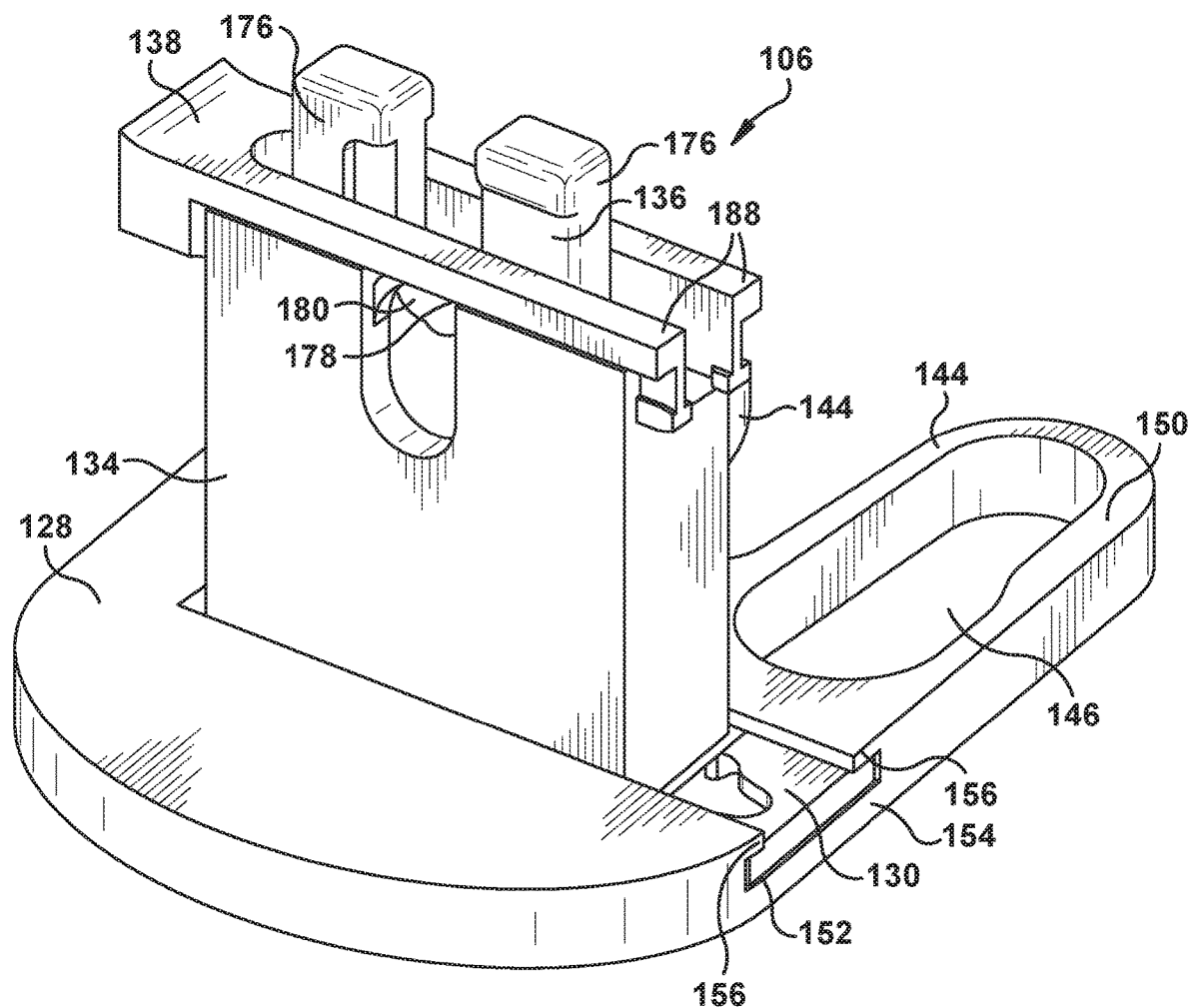
FIG. 10 is a perspective view the stabilizing device of FIG. 6.
Figure 11:
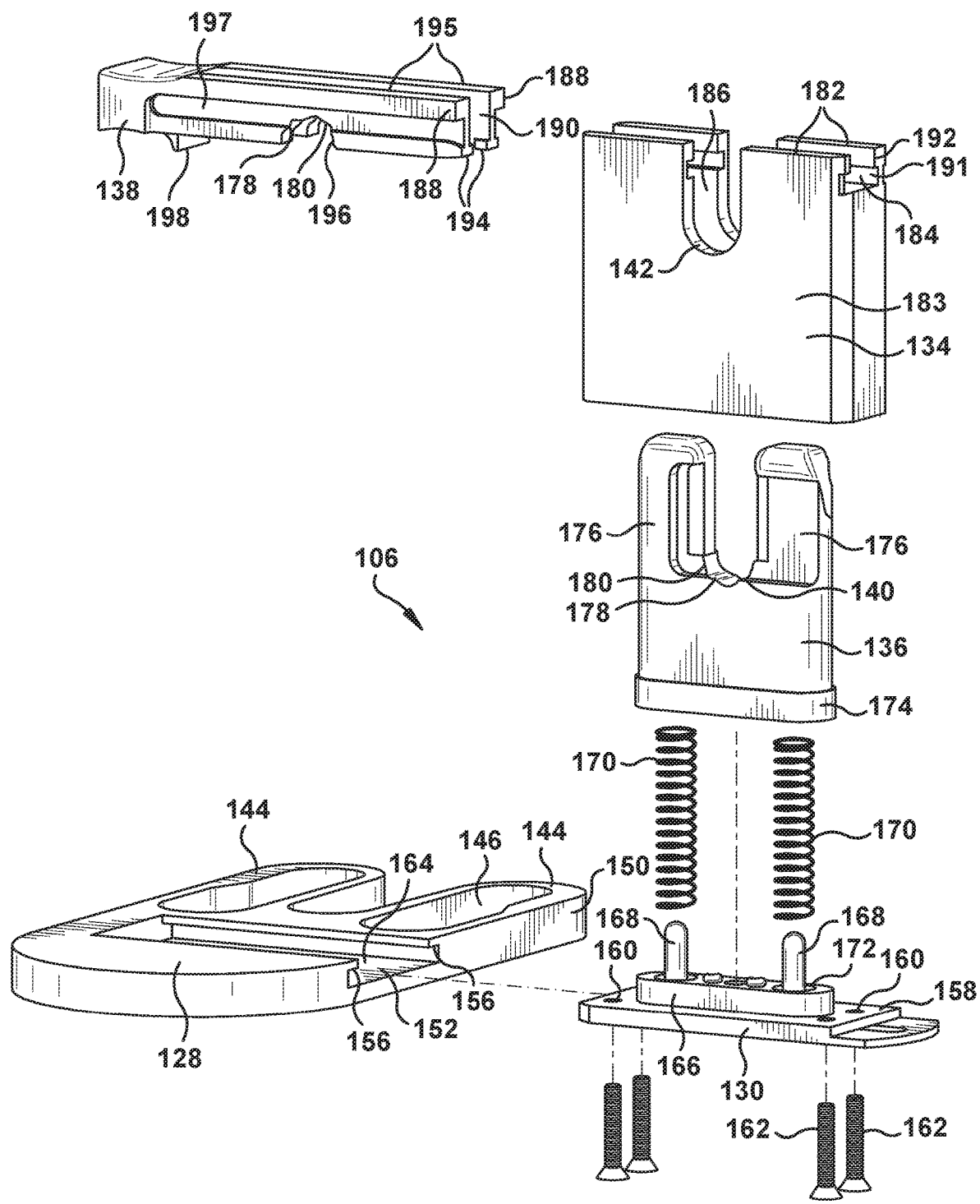
FIG. 11 is an exploded, perspective view of the stabilizing device of FIG. 6.

With reference to FIGS. 10 and 11, the stabilizing unit 106 can comprise a base member 128, a lower housing portion 130, an upper housing portion 134, a stabilizing fork 136, and a retaining arm 138. The handle 104 of the medical device 102 can be secured by a yoke formed from semicircular or U-shaped slots 140, formed in the stabilizing fork 136, and slots 196, formed in the retaining arm 138. However, the stabilizing unit can take any of the forms or have any of the features of the stabilizing units shown in FIGS. 1A-1H, 2A-2I, 3A-3I, and 4.

The base member 128 can comprise a broad, U-shaped body comprising a plurality of longitudinally extending arms 144, and a laterally extending slot 152. The body of the base member 128 can have an at least substantially planar bottom surface adapted to be mounted on the mounting surface 110 of the table 108. The arms 144 can comprise longitudinally extending cutout sections 146. In at least some cases, the cutout sections 146 can extend through the upper and lower surfaces of the arms 144 (i.e., the cutout sections extend the entire height of the arms 144). In other cases, a portion of the bottom of the base 128 can extend beneath the cutout sections 146, such that the cutout sections 146 do not extend through the bottom surfaces of the arms 144 (i.e., the cutout sections are recessed portions in the upper surfaces of the arms 144). The cutout sections 146 can be used to help secure the base member 128 to the table 108.

For example, as shown in FIG. 6, a clamp 148 can be used to secure an arm 144 to a vertical side 112 of the table 108. The width of the exterior, longitudinally extending side 150 (FIG. 10) of the arm 144 can be selected to be at least about the same as the width of the lips 114 (FIG. 6). Thus, when placed against a lateral side 112 of the table 108, the inner edge of the side 150 of the arm 144 can be at least substantially flush with the mounting ridge provided by the adjacent lip 114, which can facilitate clamping or otherwise securing the stabilizing unit 106 to the table 108. As shown in FIG. 6, one clamping arm or member 148a of the clamp 148 can be placed against the outer surface of the adjacent lateral side 112, and the other clamping arm or member 148b of the clamp can be placed against the inner surface of side 150 within the cutout section 146.

In other embodiments, rather than using a separate clamp 148, the stabilizing unit 106 can incorporate a clamping mechanism. For instance, an outer, lateral surface of an arm 144 can incorporate a clamp that can be secured to a lateral side 112 of the table 108.

Figure 7:
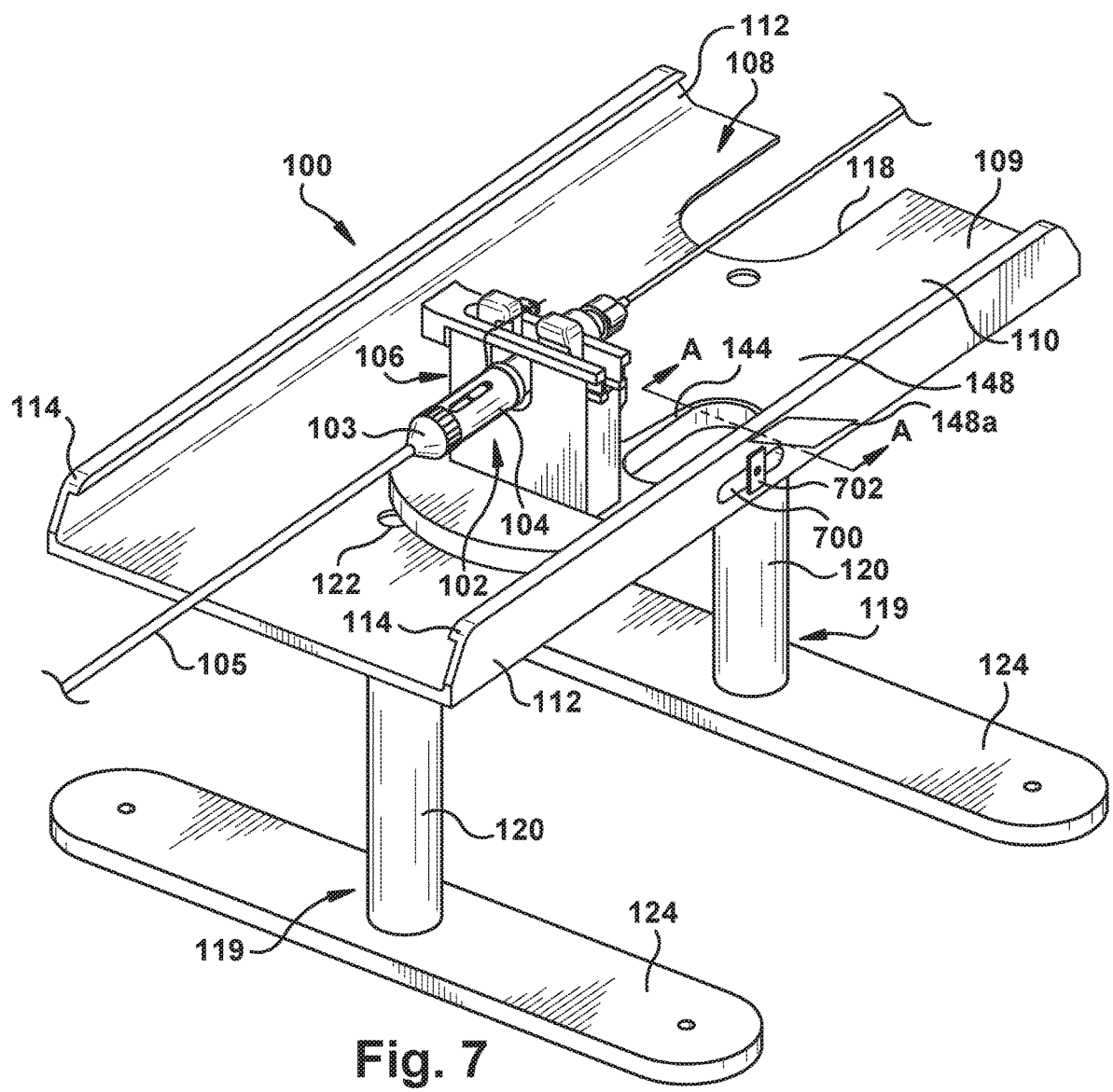
FIG. 7 is a perspective view of a support table and an example embodiment of a stabilizing unit useable with a medical device.
Figure 8:
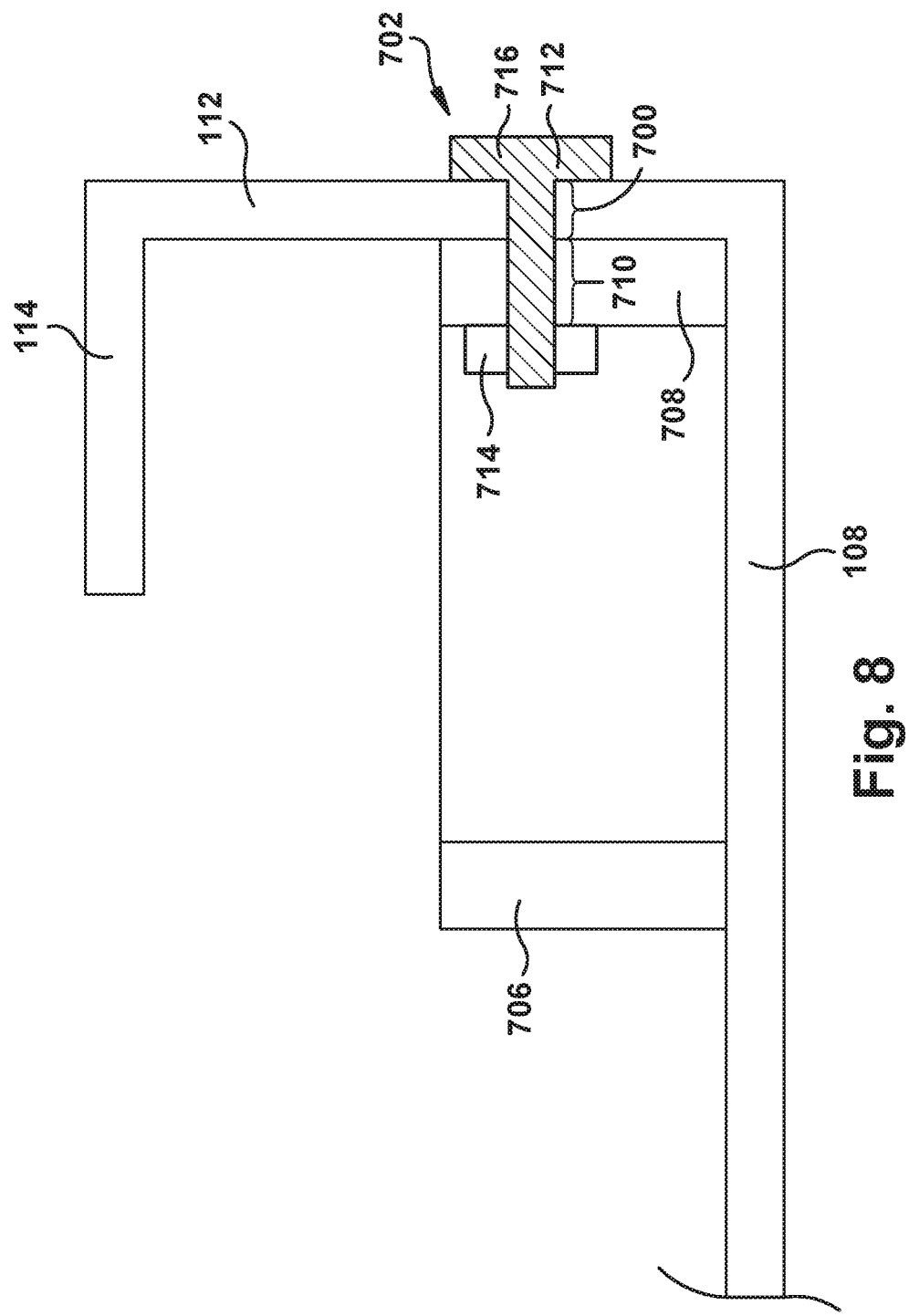
FIG. 8 is a sectional view taken along the plane indicated by lines A-A of the exemplary support table and stabilizing unit of FIG. 7.

As illustrated in FIG. 7, the lateral side 112 of the table 108 has a slot 700, a similar slot is in the outer, lateral surface of an arm 144. The incorporated clamping mechanism 702 can be placed through both slots to secure the stabilizing unit 106 to the table 108. FIG. 8 is a sectional view taken along the plane indicated by line A-A of the exemplary support table and stabilizing unit of FIG. 7. FIG. 8 shows the inner lateral surface 706 of arm 144, as well as the outer lateral surface 708 of the arm 144. The outer lateral surface 708 of the arm 144 is placed against a lateral side 112 of the table 108, which can facilitate clamping or otherwise securing the stabilizing unit 106 to the table 108. In the illustrated embodiment, the incorporated clamping mechanism 702 is placed through the slot 700 as well as the similar slot 710 located in the outer, lateral surface of an arm 144. The incorporated clamping mechanism 702 comprises a bolt 712 having a head 716 connected to an outer wall of the lateral side 112, wherein the bolt 712 is connected to a nut 714, wherein the nut is located on an inner wall of the outer surface 708 of the arm 144. The bolt traverses both slots 700, 710, which can facilitate clamping or otherwise securing the stabilizing unit 106 to the table 108.

Figure 9:
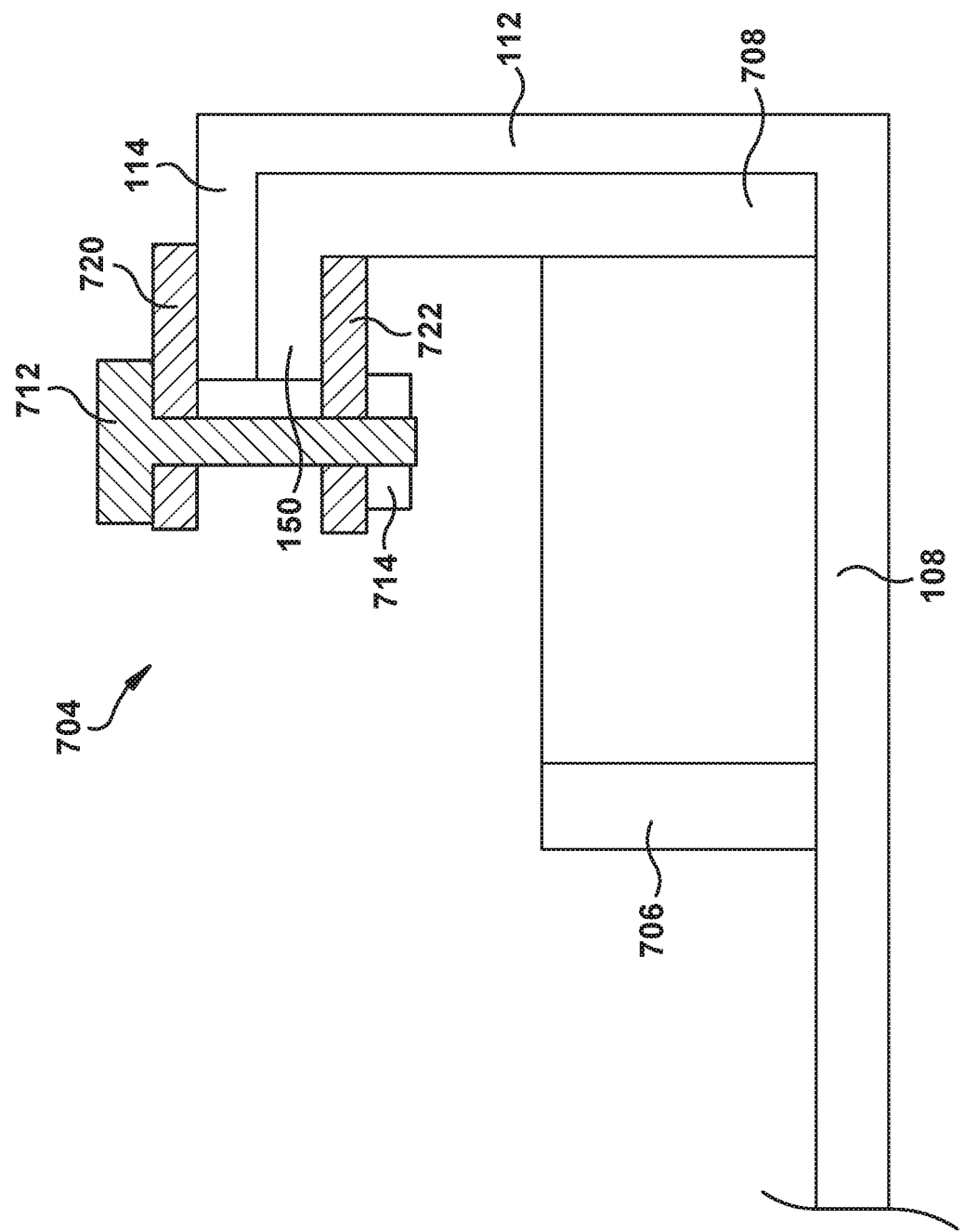
FIG. 9 is a sectional view taken along the plane indicated by lines A-A of an exemplary support table and stabilizing unit.

FIG. 9 is a sectional view taken along the plane indicated by line A-A of the exemplary support table and stabilizing unit having an alternative clamping mechanism 704. The outer lateral surface 708 of the arm 144 is placed against a lateral side 112 of the table 108. A flange 150 of the arm 144 can be at least substantially flush with the mounting ridge provided by the adjacent lip 114, which can facilitate clamping or otherwise securing the stabilizing unit 106 to the table 108. The alternative clamping mechanism 704 comprises a bolt 712 having a head 716 connected to a first clamp side 720. The first clamp side 720 is flush against the adjacent lip 114. The alternative clamping mechanism 704 further comprises a second clamp side 722, which is flush against the flange 150 of the arm 144. The bolt 712 is connected to a nut 714, wherein the nut is located on the flange 150 of the arm 144. The bolt traverses the first and second clamp sides 720, 722. The alternative clamping mechanism 704 facilitates clamping or otherwise securing the stabilizing unit 106 to the table 108.

In yet other embodiments, a clamp need not be used with the stabilizing unit 106. If desired, a bottom surface of the stabilizing unit 106 can be formed from a material with a large coefficient of friction, or pads of a material with a large coefficient of friction can be attached (such as being adhered) to a bottom surface of the stabilizer unit. The stabilizing unit 106 can be constructed from a material having a weight sufficient to help retain the stabilizing unit at a desired position on the table 108.

As best shown in FIG. 11, the laterally extending slot 152 can extend from one side 154 of the base member. The slot 152 can have a reduced width proximate the top of the base member 128, defining longitudinally extending ridges 156. The lower housing portion 130 can be disposed within the slot 152. The lower housing portion 130 can have a width greater than the gap between the ridges 156. Thus, when inserted into the slot 152 through the side 154 of the base member 128, the lower housing portion 130 can be secured against upward movement relative to the base member and against movement perpendicular to the length of the slot 152.

The lower housing portion 130 can comprise a lower portion 158, an upper mounting section 166, and a plurality of vertical post members 168. As best shown in FIG. 11, the lower portion 158 can comprise a plurality of apertures 160 that extend from the upper surface of the lower portion 158 through a bottom surface of the lower portion 158. Each of the apertures 160 can receive a fastener 162, such as the illustrated screw. The fasteners 162 can be received by threaded apertures (not shown) of the upper housing portion 134. The fasteners 162 can thus secure the lower housing portion 130 and upper housing portion 134 to one another.

As further shown in FIG. 11, the mounting section 166 can extend upwardly from the upper surface of the lower portion 158, and can have an obround horizontal cross sectional shape, although other shapes can be used (e.g., rectangular). The post members 168 can extend upwardly from the mounting section 166, such that the longitudinal axes of the post members are orthogonal to the upper surface of the mounting section. Each post 168 can be configured and dimensioned to receive a biasing member 170, such as the illustrated coil spring. Each post 168 can extend coaxially through the lower end portion of a respective biasing member 170. Each post 168 can be encircled by a well or recessed portion 172 formed in the upper surface of the mounting section 166 and configured to receive a lower end portion of a respective biasing member 170. The wells 172 can assist in maintaining the position of their respective biasing members 170 relative to a respective post member 168 and the mounting section 166. The upper end portion of each biasing member 170 can extend through a respective aperture (not shown) formed in a bottom surface of the stabilizing fork 136 and can bear against an inner surface within the stabilizing fork 136. In this manner, the biasing members 170 apply a biasing force that biases the stabilizing fork 136 away from the lower housing 130.

The stabilizing fork 136 can comprise an enlarged lower portion 174 dimensioned to fit over the mounting section 166 of the lower housing portion 130. For example, the lower portion 174 can extend around the mounting section 166, abutting the upper surface of the lower portion 158 of the lower housing, when the stabilizing fork 136 is depressed downwardly by a user wishing to adjust the position of a medical device secured thereby, as further described below In at least some aspects, the height of the mounting section 166 and the height of the lower portion 174 can be selected based on the desired degree of travel of the stabilizing fork 136 between its compressed and released positions. That is, the heights can correspond to the degree of travel of the stabilizing fork.

The stabilizing fork 136 can comprise arms 176 separated by the U-shaped slot 140. The base of the slot 140 can comprise a plurality of ridges 178 extending transversely between the vertical faces of the stabilizing fork 136. The ridges 178 can define scalloped mounting recesses 180 that can be configured to engage surface features of a medical device, such as the handle 104 of the catheter 103, to help secure the handle against rotational movement relative to the stabilizing fork 136.

The upper housing portion 134 can comprise longitudinally extending U-shaped slots 142 formed in the vertical side walls 183 of the upper housing portion and a laterally extending inverted T-shaped slot 184 formed in the upper end portion of the upper housing portion. The U-shaped slots 142 can have at least approximately the same width as the U-shaped slot 140 of the stabilizing fork 136. The inverted. T-shaped slot 184 can have an upper portion 192 (the stem of the T) having a width smaller than the width of a lower portion 191 (the crossbar of the T). The side walls 183, the sides of the slot 184 and the upper ends 182 of the upper housing portion 134, can be spaced apart to provide a vertical aperture 186 between the faces through which the arms 176 of the stabilizing fork 136 can extend.

The retaining arm 138 can comprise guide rails 188, the slot 196, and a stop 198. The slot 184 can be configured to receive lower portions 194 of the guide rails 188 of the retaining arm 138. The lower portions 194 are configured to extend into recesses of the slot 194 formed by the lower portion 191 of the slot 184. Upper portion 195 of the guide rails 188 are configured to abut the upper ends 182 of the upper housing portion 134. The upper 195 and lower 194 portions of the guide rails 182 can have a larger width than an intermediate portion of the guiderails, forming an outwardly facing groove 197.

The guide rails 188 can be spaced apart to provide an aperture 190 through which the upper end portions of the arms 176 of the stabilizing fork 136 can extend. An upper portion 192 of the slot 184 can have a smaller width than the lower portion 194 and upper portion 195 of the guide rails 188, thus preventing the guide rails from being removed from the slot by moving them upwardly, away from the upper housing portion 134. That is, the groove 197 can be slid over the upper portion 192 of the slot 184.

The stop 198 can extend downwardly from a bottom surface of the retaining arm. The stop 198 can be configured to engage a lateral side of the upper housing portion 134, limiting movement of the retaining arm 138 relative to the upper housing portion.

The guide rails 188 can define the semi-circular (or, in some cases, U-shaped) slots 196. The slots 196 can comprise ridges 178 and mounting recesses 180 like the slot 140 of the stabilizing fork 136. The slots 196 of the retaining arm 138 can cooperate with the slots 142 of the upper housing portion 134 and the slot 140 of the stabilizing fork 136 to form a yoke useable to secure a medical device placed therethrough.

In use, the support members 119 can be placed on an operating table, with the legs 120 between a patient's legs. The patient's legs can be placed over the feet 124 to help secure the table 108. The stabilizing unit 106 can be placed on the support surface 110 of the table 108. The stabilizing unit 106 can be moved to a desired longitudinal position on the support surface 110 and moved laterally to abut a lateral side 112 of the table 108. The stabilizing unit 106 may then be secured in position, such as by attaching the clamp 148 about the side 150 of the outer arm 144 of the base 128 and the outer surface of the lateral side 112. The side 150 of the arm 144 can be positioned beneath the lip 114 such that the inner edge of the recess 146 and the outer edge of the lip are flush, which can help provide a uniform clamping surface for the clamp 148. Although one clamp 148 is shown in FIG. 6, in practice, multiple clamps can be used, or the stabilizing unit 106 secured to the table 108 by other means.

The retaining arm 138 of the stabilizing unit 106 can be removed from the stabilizing unit, or retracted from the slot 184 of the upper housing portion 134 so as to allow the handle 104 of the catheter 103 to be placed in the slots 140 and 142. While the handle 104 is being placed in the slots 140 and 142, the stabilizing fork 136 can be manually depressed toward the lower housing portion 130 against the biasing force of the biasing members to move the slot 140 lower relative to upper housing portion 134. With the handle 104 inserted within the slots 140 and 142, the retaining arm 138 can be slid toward the upper housing portion 134 to place the slots 196 over the slots 140 and 142. Manual pressure on the stabilizing fork 136 can then be released, which allows the biasing members 170 to push the lower surface of the slot 140 against a lower circumferential surface of the handle 104 of the catheter 103 and an upper circumferential surface of the handle 104 against the slots 196. The upwardly directed force of the biasing members 170 holds the handle of the catheter between the stabilizing fork and the stabilizing arm and resists against inadvertent axial and rotational movement of the catheter relative to the stabilizing unit. The ridges 178 and mounting recesses 180 can mate with corresponding features on the handle 104 to help secure the handle against rotational movement within the slots 140 and 196.

If an operator desires to adjust the position of the medical device 102 (the axial and/or rotation position of the medical device), the operator can manually depress the stabilizing fork 136 to move the slot 140 out of engagement with the handle 104. While maintaining the compressive force against the stabilizing fork 136, the operator can adjust the position of the catheter handle 104, including rotating it or moving it distally or proximally relative to a patient. When the operator is satisfied with the position of the medical device 102, the operator can remove the compressive force from the stabilizing fork 136, whereby the biasing members 170 will again urge the stabilizing fork 136 upwardly such that the slot 140 abuts the handle 104, securing the handle between the slot 140 and the slots 196 of the retaining arm 138. The operator can repeat this adjustment as desired during a medical procedure.

Although one stabilizing unit 106 is shown placed on the table 108, plural stabilizing units 106 can be placed on the same table 108 and used to secure respective medical devices during a medical procedure. For example, if the medical assembly includes multiple catheters inserted coaxially through one another, the stabilizing units 106 can be placed one behind the other along the length of the platform 108, with the handle of each catheter mounted in one of the stabilizing units. In another example, if the medical assembly includes multiple catheters placed side-by-side, the stabilizing units 106 can be placed side-by-side or laterally spaced across with the width of the platform 108, with the handle of each catheter mounted in one of the stabilizing units.

Figure 12:
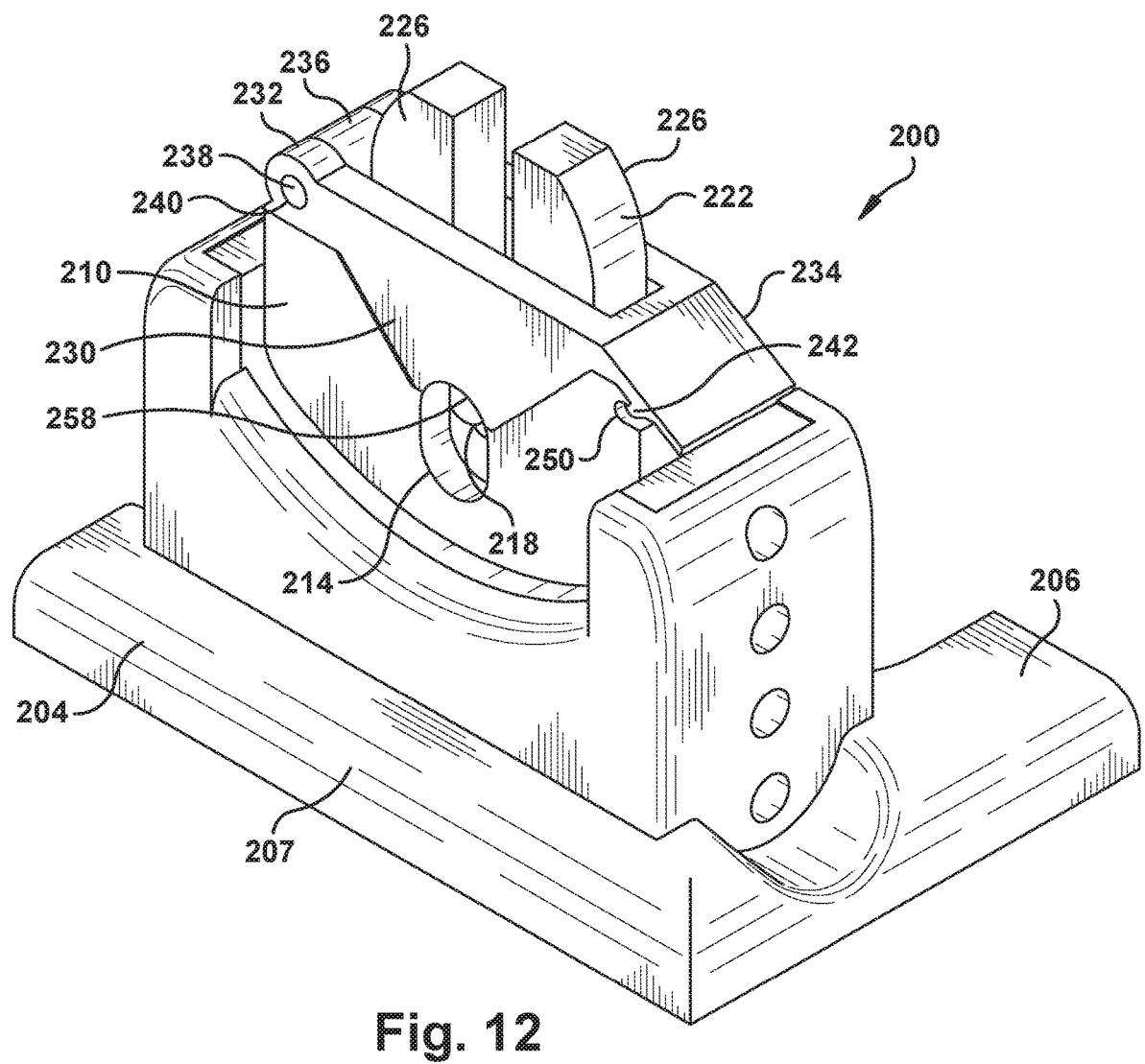
FIG. 12 is a perspective view of another example embodiment of a stabilizing device useable with a medical device.

FIG. 12 illustrates another example of a stabilizing unit 200 that can be used with the medical device 102 and the table 108 of FIG. 6. The stabilizing unit 200 can comprise a base member 204, a housing 210, a stabilizing fork 222, and a pivotable retaining arm 230. The base member 204 can have arms 206 (one of which is visible in FIG. 12) extending rearwardly from an elongate portion 207 of the base member. Although not shown in FIG. 12, in some cases, the arms 206 can comprise cutout sections, analogous to the cutout sections 146 of the arms 144 of the base member 128 of FIG. 10. The cutout sections can be used to help secure the stabilizing unit 200 during a medical procedure, such as by clamping the stabilizing unit to a support table.

The housing 210 can define vertical, U-shaped slots 214 formed in the front and rear vertical side walls of the housing. The U-shaped slots 214 can be aligned with a U-shaped slot 218 formed in the stabilizing fork 222. The U-shaped slot 218 can define vertically extending arms 226 of the stabilizing fork 222, which can extend upwardly through the retaining arm 230. The stabilizing fork 222 can be mounted in a space between the opposing front and rear vertical side walls of the housing 210.

The pivotable retaining arm 230 can comprise a mounting end portion 232 and an actuating tab 234. The mounting end portion 232 can be hingeably connected to a mounting projection 236 extending vertically from a lateral side of the upper end of the housing 210. For example, the mounting end portion 232 can be connected to the mounting projection 236 using a pin 238 or similar coupling mechanism inserted through apertures 240 formed in the mounting end portion 232 lone of which is shown in FIG. 12) and a mating aperture formed in the mounting projection 236 (not visible in FIG. 12).

The actuating tab 234 can define a tongue 242 inwardly extending toward the lower end of the housing 210 from a lower surface of the actuating tab. The upper end portion of the housing 210 can define a groove 250 for receiving the tongue 242, allowing the retaining arm 230 to be releasably secured to the housing 210.

The lower longitudinal surface of the retaining arm 230 can define a semi-circular (or, in some cases, U-shaped) slots 258. The slots 258 of the retaining arm 230, the slots 214 of the housing 210, and the slot 218 of the stabilizing fork 222 can cooperate to form a yoke that can abut a medical device extending therethrough. The stabilizing fork 222 can be biased towards the retaining arm 230, such as using springs or other biasing members, which can be placed in contact with the stabilizing fork in a similar manner as the biasing devices 170 and the stabilizing fork 136 of FIGS. 10 and 11.

The stabilizing unit 200 can be used in a similar manner as the stabilizing unit 106. When a medical device is to be inserted into the unit 200, the tongue 242 can be removed from the groove 250 by pulling the actuating tab 234 and pivoting the retaining arm 230 away from the housing 210. The stabilizing fork 222 can be manually depressed, and the medical device can be inserted within the slots 214, 218. The retaining arm 230 can then be pivoted toward the housing 210 and the tongue 242 secured within the groove 250. The compressive force on the stabilizing fork 222 can be removed, allowing the stabilizing fork to move upwardly towards the retaining arm 230, and urging the slot 218 against the lower surface of the medical device, and in turn pushing the medical device against the bottom of the slots 258. The position of the medical device can be adjusted by again manually depressing the stabilizing fork 222 such that the slot 218 is moved out of engagement with the medical device.

Components of a stabilizing system, such as the medical device 102, the stabilizing unit 106 (or the unit 200), and the table 108, are typically shipped to a location (such as a clinic or hospital) where a medical procedure is to be performed. In at least some cases, the packaging used to ship or store system components can be used to construct all or a portion of other system components. In particular, packaging can be used to construct all or a portion of a table on which a stabilizing unit can be placed.

FIGS. 13A-13C illustrate a packaging sheet 300 in which a medical device, such as an introducer sheath or a guide sheath, can be shipped to a location (such as being shipped within a box, carton, or other type of packaging). The packaging sheet 300 can comprise a recess 308 for receiving a handle 304, the medical device, a plurality of support members 312, and a plurality of retaining members 324, such as brackets or straps. The packaging sheet can be constructed from a sterilizable, suitably rigid material, such as polycarbonate or high density polyethylene (HDPE). The recess 308 can be configured and dimensioned to hold the medical device 304 and protect it from damage during transit.

The support members 312 can be pivotable relative to the sheet 300 and can each have an upper leg 320 and a lower leg 326 connected to each other by a connecting post 322. The upper leg 320 of each support member 312 can be secured to a bottom surface 316 of the packing sheet 300 by the retaining members 324, which can be secured to the bottom surface of the packaging sheet, such as with a suitable adhesive, by welding, and/or fasteners. Although not shown, in a shipping and storage configuration 328, the lower leg 326 of one or both of the support members 312 can be disposed over a portion of the recess 308, thus helping secure the handle 304 of the medical device within the recess and protecting it from damage.

With reference to a use configuration 332, when the medical device 304 is to be used, or the packaging sheet 300 is otherwise desired to be converted to a table for use in a medical procedure, the support members 312 can be pivoted by rotating the lower legs 326 outwardly such that the support members 312 extend vertically from the bottom surface 316 of the packaging sheet 300.

The packaging sheet 300 can be turned over and the lower legs 326 placed on a supportive surface, such as an operating table (not shown) to provide an unfolded and operative configuration 340, as shown in FIG. 13C. One or more stabilizing units 344, such as the stabilizing unit 106 of FIG. 1A-6 or the stabilizing unit 200 of FIG. 12, can be placed on an upper surface 348 of the packaging sheet 300. The upper surface 348 can provide a support surface for the stabilizing units 344. The medical device 304 can be mounted on the stabilizing unit 344.

Figure 14A:
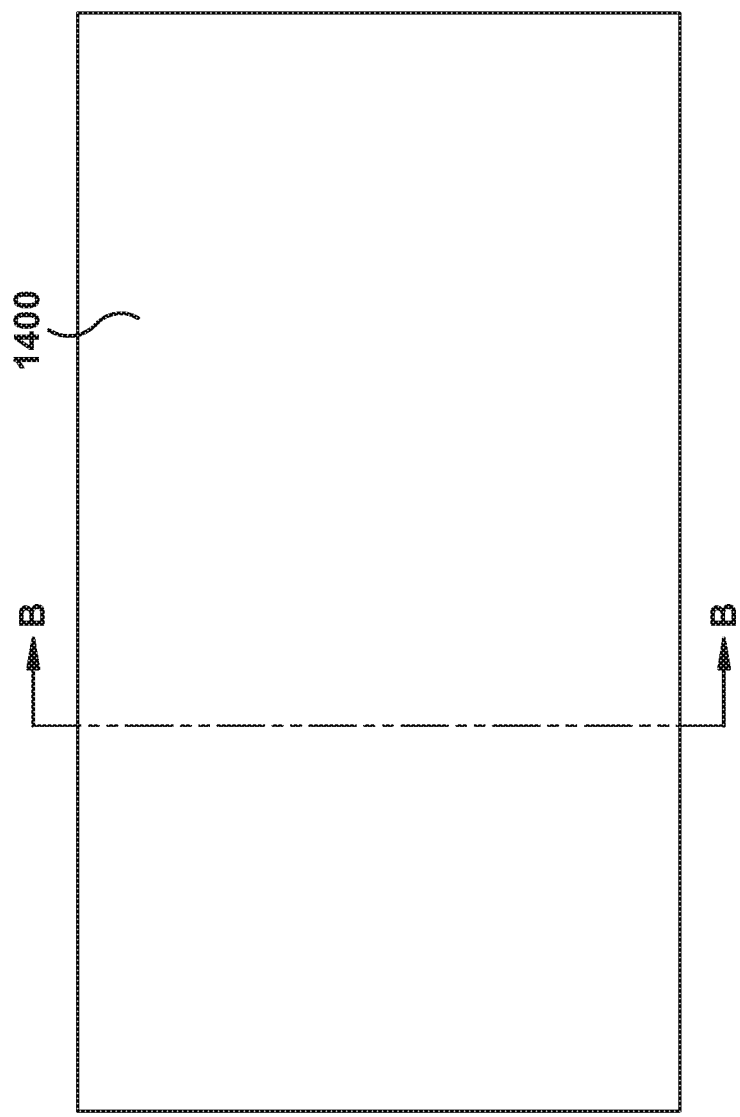
FIG. 14A is a schematic view of an exemplary embodiment of medical device packaging.
Figure 14B:
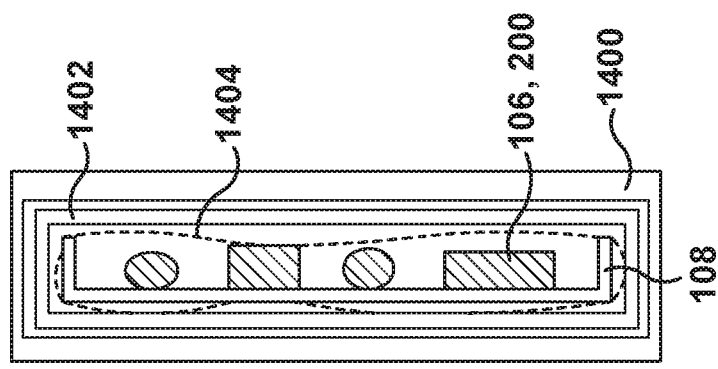

FIG. 14A illustrates another embodiment of the packing for the medical device that includes a shipping box 1400. FIG. 14B is a sectional view taken along the plane indicated by line B-B of the exemplary shipping box 1400 of FIG. 14A. The shipping box 1400 contains at least the components of a stabilizing system, such as the medical device 102, the stabilizing unit 106 (or the unit 200), and the table 108. In certain embodiments, the shipping box can contain more or fewer components than are illustrated in FIG. 13A. In certain embodiments, an inner box 1402 may be located inside the shipping box 1400. The shipping box 1400 may also include pouch 1404 that includes all the sterile items. However, any of the pieces inside the shipping box 1400 may be sterile.

FIGS. 15A-15C illustrate another embodiment of packaging sheet 300 in which a medical device can be shipped to a location. The packaging sheet 300 can comprise a recess 308 for receiving a handle 304 the medical device, a second recess 1308 for receiving a stabilizing apparatus 10, a plurality of support members 312, and a plurality of retaining members 324, such as brackets or straps. The packaging sheet can be constructed from a sterilizable, suitably rigid material, such as polycarbonate or high density polyethylene (HDPE). The second recess 1308 can be configured and dimensioned to hold the stabilizing apparatus 10 and protect it from damage during transit. In the illustrated embodiment, the stabilizing apparatus 10 is folded to a compact position and positioned in the second recess 1308.

Figure 16:
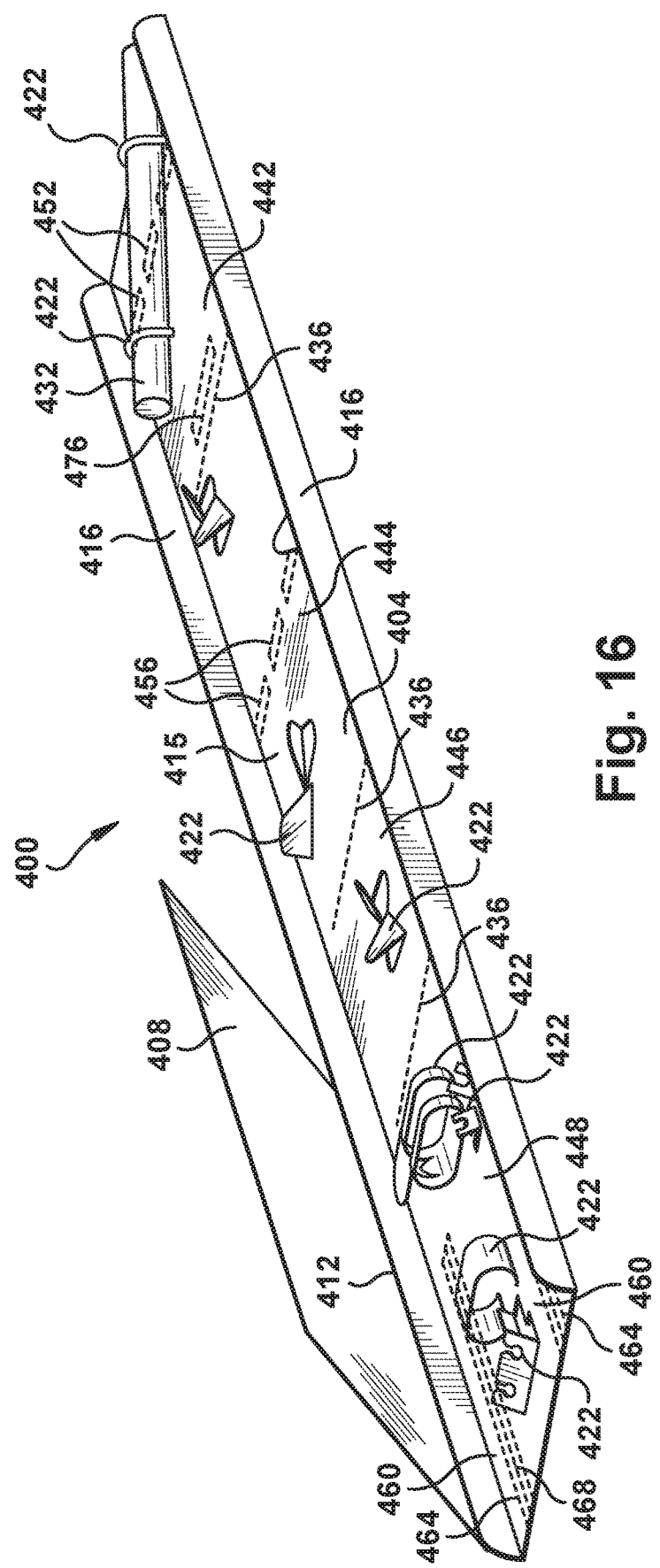
FIG. 16 is a perspective view of exemplary medical device packaging that can be used to construct a support table for a medical device.
Figure 17:
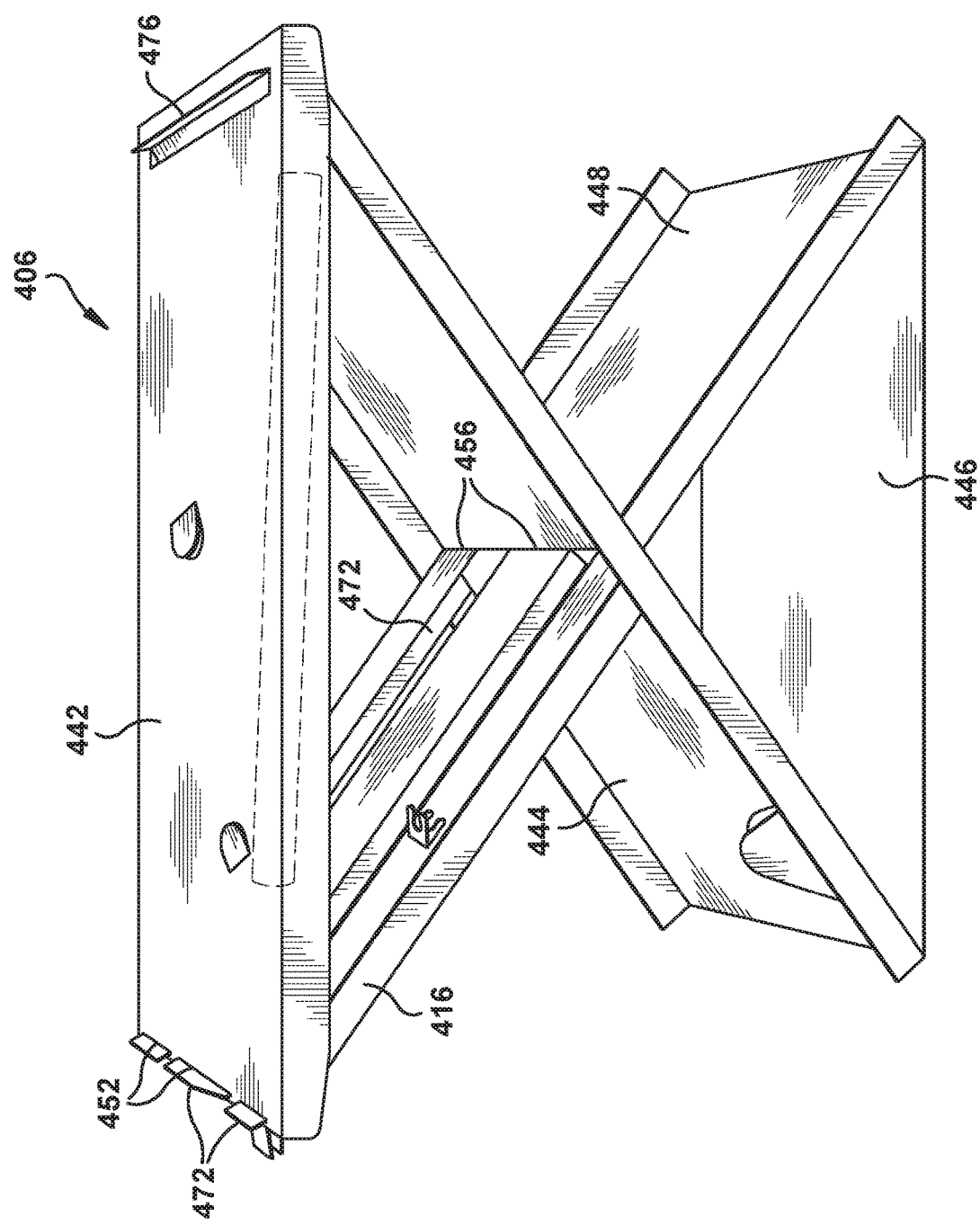
FIG. 17 is a perspective view of a support table formable from the packaging of FIG. 16.

FIG. 16 illustrates another example of a packaging sheet 400 that can be used to construct all or a portion of a table or platform 406, shown in FIG. 17, on which a stabilizing unit (e.g., the stabilizing unit 106 or the stabilizing unit 200) can be placed. The packaging sheet 400 can comprise a base 404, a flap 408, longitudinal ridges 416, a plurality of retaining members 422, a plurality of fold points 436, slots 452, 456, and tabs 460. Like the packaging sheet 300, the packaging sheet 400 can be constructed from a sterilizable, suitably rigid material, such as polycarbonate or high density polyethylene (HDPE). The base 404 can be elongate, generally planar, and generally rectangular.

The flap 408, which can be generally rectangular, can extend from the side of a longitudinal end portion of the base 404. The flap 408 can be used, for example, to help protect components (such as a prosthetic valve, a delivery assembly for a prosthetic valve, a stabilizing unit, or components thereof) from damage during transit. In some cases, the flap 408 can be removed prior to constructing the table 406 from the packaging sheet 400. The flap 408 can be cut or torn off, for example, and the flap can comprise features to assist in its removal. A side 412 of the flap 408 extending from the base 404 can comprise perforations, scoring, or creases to assist in removing the flap from the base. In other cases, the flap 408 can be folded behind the base 404 and used to help provide structural support to the table 406, such as by making a span of the table 406 more rigid.

The longitudinal ridges 416 can extend vertically from, and orthogonally to, a horizontal portion 415 of the base 404. The ridges 416 can be formed by folding the sides of the base 404. The base 404 can comprise creases or other features to aid in forming the ridges 416. In other cases, the packaging sheet 400 can comprise preformed ridges 416, such as being molded to comprise both the horizontal portion 415 and the ridges.

The retaining members 422, such as flaps, loops, straps, and notches, can be formed from, or coupled to, the base 404. The retaining members 422 can be used to help secure and organize components of a prosthetic valve, delivery assembly, or stabilizing unit during transit. For instance, retaining members 422 (e.g. loops) can be used to secure a tube 432. The tube 432 can be used to house a prosthetic valve within a storage tube (not shown). Other retaining members 422 (e.g., straps and notches) can be used to secure components of a delivery assembly, such as a guide sheath (e.g., the guide sheath 304 of FIG. 13) and tubes and shafts extending therefrom.

The base 404 can be folded at the fold points 436, which can extend laterally across the base, to construct the table 406. The fold points 436 can be creased, scored, or perforated to assist a user in identifying the correct fold location, folding the base 404 in the correct direction, and allowing the base to fold more easily about a fold point. In the illustrated embodiment, the base 404 comprises three fold points 432. The fold points 436 can divide the base into a plurality of segments 442, 444, 446, and 448. Depending on how the table 406 is constructed, more or fewer fold points 436 can be included or used. For example, the base 404 can produce a U-shaped table using two fold points.

In some configurations of a table 406, one of the segments may need to pass through, or be secured to, another segment. For example, with additional reference to FIG. 17, an end portion of segment 448 can be configured to be inserted through the slots 452, formed in an end portion of segment 442, and the slots 456, formed in a midsection of segment 444. Returning to FIG. 16, in some cases, the slots 452, 456 can be pre-formed (such as precut) in the segments 442, 444. In other cases, the slots 452, 456 can be formed by cutting or otherwise removing material from the segments 442, 444 during assembly of the table 406. For instance, the segments 442, 444 can comprise scored or perforated lines defining the slots 452, 456. During table assembly, a user can punch out the perforated or scored material to produce the slots 452, 456.

As shown best in FIG. 6, segment 448 can comprise the tabs 460, which can be inserted into mating slots 452, 456. The tabs 460 can be formed by folding the material of the segment 448 or by removing material from the segment. As shown, each tab 460 can comprise longitudinally extending fold lines 464. A longitudinal slit 468 can be formed between the fold lines 464. For example, the slit 468 can be cut by a user, or can be pre-formed in the segment 448 (such as by precutting the slit, or including perforations or scoring to assist a user in forming the slit). When the table 406 is assembled, the lateral sides of the tabs 460 can be folded about the longitudinal axis of the base 404, and the tabs thereby formed can be inserted through the slots 452, 456. After being inserted through the slots 452, 456, the material of the segment 448 folded about the tabs 460 can be unfolded, with the widened portions 472 (FIG. 17) helping to prevent the tabs from slipping back through the slots.

In another aspect, rather than folding the segment 446 to produce the tabs 460, strips of material (e.g., the material between the fold lines 464) can be removed from the segment 448 to form the tabs. In order to facilitate the removal of the strips of material, the fold lines 464 can be scored or perforated.

The segment 442 can define a flap 476. The sides of the flap 476 can be creased, scored, or perforated to help a user fold the flap out (e.g., by rotating the flap about a lateral axis of the base 404) during table assembly. The flap 476 can be used to help secure a stabilizing unit to the table 406 during a medical procedure.

FIG. 17 illustrates the table 406 in its assembled form. Segment 444 has been folded at least approximately 135 degrees clockwise, beneath segment 442. Segment 446 has been folded at least approximately 135 degrees clockwise, beneath segment 444, such that segment 446 is disposed below, and parallel to, segment 442. The ridges 416 of segment 446 can be folded over or underneath (e.g., about the longitudinal axis of segment 446) the segment. Segment 448 has been folded at least approximately 135 degrees clockwise, above segment 446.

Segment 448 can intersect segment 444 at least approximately at the longitudinal midpoint of segment 444. The tabs 460 of segment 448 are shown inserted through the slots 456 of segment 444 and the slots 452 of segment 442. The ridges 416 are shown as downwardly folded after passing upwardly through the slots 456. The downwardly folded ridges 416 can provide widened portions 472 that can help prevent the tabs 460 from sliding back through the slots 456, helping to make the table 406 more rigid and secure. Similarly, the widened portions 472 proximate the slots 452 can help prevent the tabs 460 from sliding back through the slots.

The flap 476 is shown as extending upwardly from the surface of the segment 442. A stabilizing unit can be placed on the surface of the segment 442, which provides a support surface, and secured to the flap 476. For example, a stabilizing unit can be secured to the flap 476, in an analogous manner to how the stabilizing unit 106 of FIG. 6 is secured to the lip 114 of the table 108 using the clamp 148. Segment 446 can provide a support member of the table 406.

The use of packaging to produce tables or platforms for a medical device (such as a stabilizing unit) can provide a number of advantages. For instance, it can be less wasteful of material, and less expensive, than providing a table as a separate, discrete component. In addition, the table, at least in part because of its inexpensiveness, can be a single-use, disposable component. Although a single table is shown, packaging can be provided to provide multiple tables, one or more of which can be used in a medical procedure.

Figure 18:
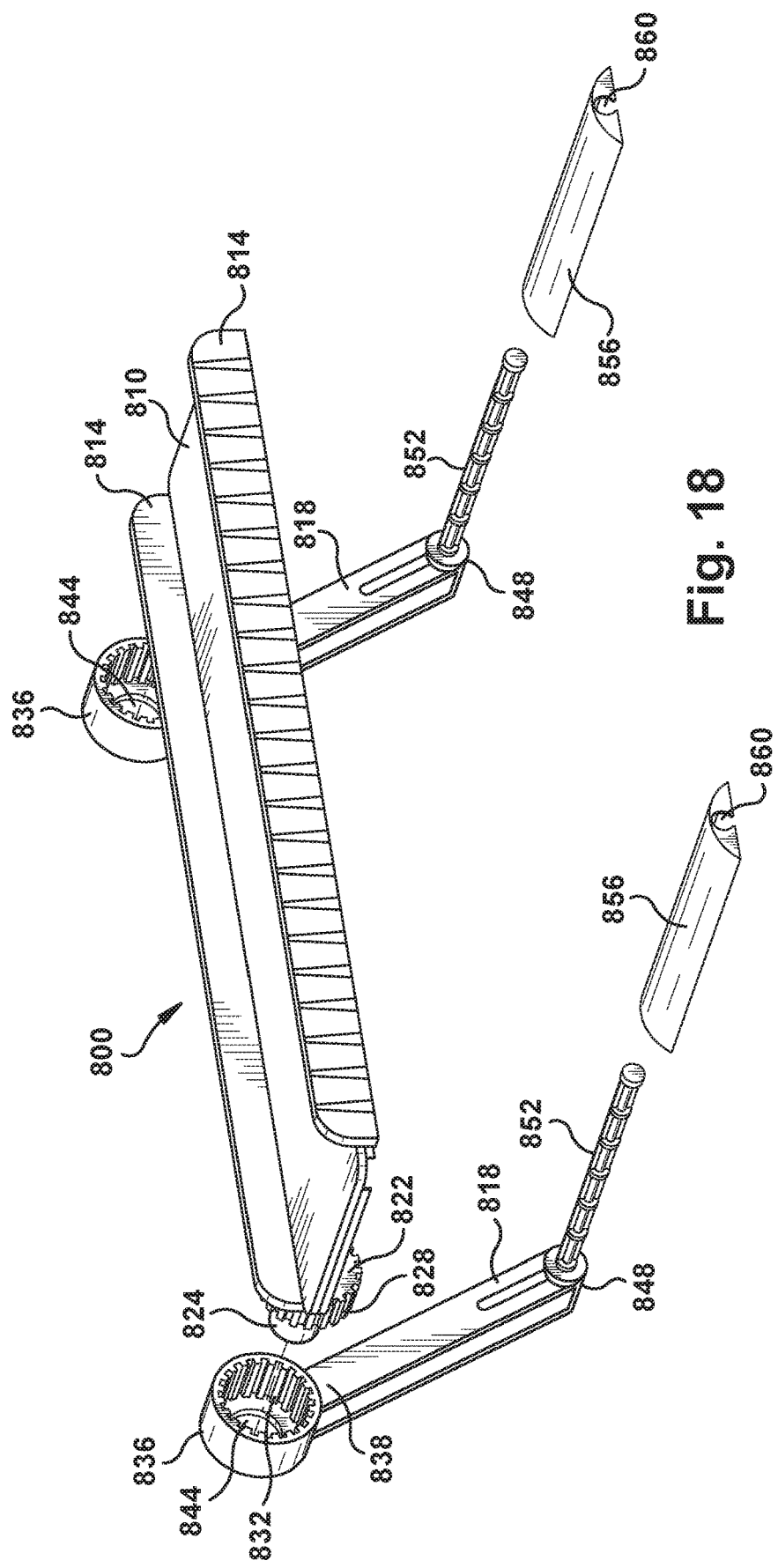
FIG. 18 is a perspective view of another example embodiment of a support table that can be used with a medical device and/or a stabilizing unit therefor.

FIG. 18 illustrates another example of a table 800 that can be used with a medical device or a support therefor, including the stabilizing unit 106 of FIG. 1A-6 or the stabilizing unit 200 of FIG. 12. The table 800 has an elongate surface 810, two lateral sides 814, extending vertically from the elongate surface, and a plurality of support members, or legs, 818. If desired, the lateral sides 814 can incorporate a lip, which can be analogous to the lip 114 of the table 108 of FIG. 6. Although the elongate surface 810 and lateral sides 814 are shown as unitary, contiguous surfaces, the elongate surface, lateral sides, or both, may be constructed from multiple pieces which can be secured together. For instance, the elongate surface 810 can be formed from two, or more, hingeably coupled pieces, or multiple pieces can be joined in a snap-fit fashion.

The table 800 can include a plurality of coupling members 822 (one of which is visible in FIG. 18). The coupling members 822 can extend laterally from one or both of the lateral sides 814 of the table 800, and can be integrally formed with the lateral sides, or coupled to the lateral sides, such as by welding, adhesion, or the like. The coupling members 822 can include a cylinder or rod 824 that extends laterally, axially outwardly from a toothed ring 828. The teeth of the toothed ring 828 can be configured to matingly engage teeth 832 formed on a radial internal surface of an annular receptacle 836 disposed at an upper end 838 of each support member 818. The receptacles 836 can have an inner dimension selected to receive the toothed ring 828, and can include an axial opening 844 dimensioned to receive the cylinder 824 of a coupling member 822.

In some implementations, the receptacles 836 can be selectively detached from the coupling members 822, and the coupling members can be maintained at a fixed position with respect to the lateral sides 814 (e.g., the coupling members do not rotate), or the coupling members can be maintainable at a fixed position they can be locked at a desired position). Thus, the height and angle of the elongate surface 810 of the table 800 can be adjusted by manipulating the position of the support members 818 relative to the lateral surface, and then inserting the receptacles 836 over their respective coupling member 822 when the lateral surface is at a desired position. The height of the elongate surface 810 can be adjusted, but maintained in a horizontal position, by rotating the support members 818 relative to the elongate surface, but maintaining the support members at the same rotational position. If the table 800 is desired to be maintained at an angled, or slanted, position, one of the support members 818 can be rotated to a different degree than the other support member.

An arm 852 can extend from a lower end 848 of each support member 818. A foot 856 can be disposed about each of the arms 852, such as by inserting a respective arm through an opening 860 axially formed in the arm. The feet 856 can be rotatable relative to the arms 852, such that the feet can rest on a surface, such as a horizontal surface, even when the support members 818 are not maintained in a vertical orientation. The feet 856 can be formed from a resilient material, such that a patient may comfortably lay on the feet, helping secure the table 800 in a desired position.

Various modifications can be made to the table 800. For instance, one or both of the coupling members 822 and the receptacles 836 can be rotatable. When one or both of the coupling members 822 and the receptacles 836 are rotatable, the components may be secured to one another, or be an integral component, if desired. A locking/release mechanism, such as a spring loaded pawl, can be used to engage teeth associated with the support members 818 in order to maintain each support member at a desired position. In some embodiments, the upper end portion of each support member 818 can be pivotably connected to the table 800, such as via a pivot pin extending through the upper end portion of each support member 818 and an adjacent portion of the table.

Figure 19B:
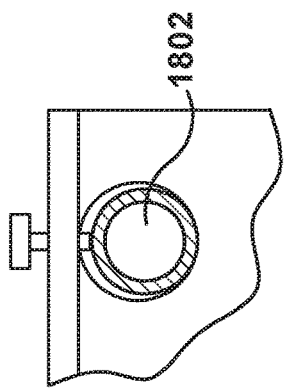
FIG. 19B is a close-up view of a portion of the support table of FIG. 19A.
Figure 19A:
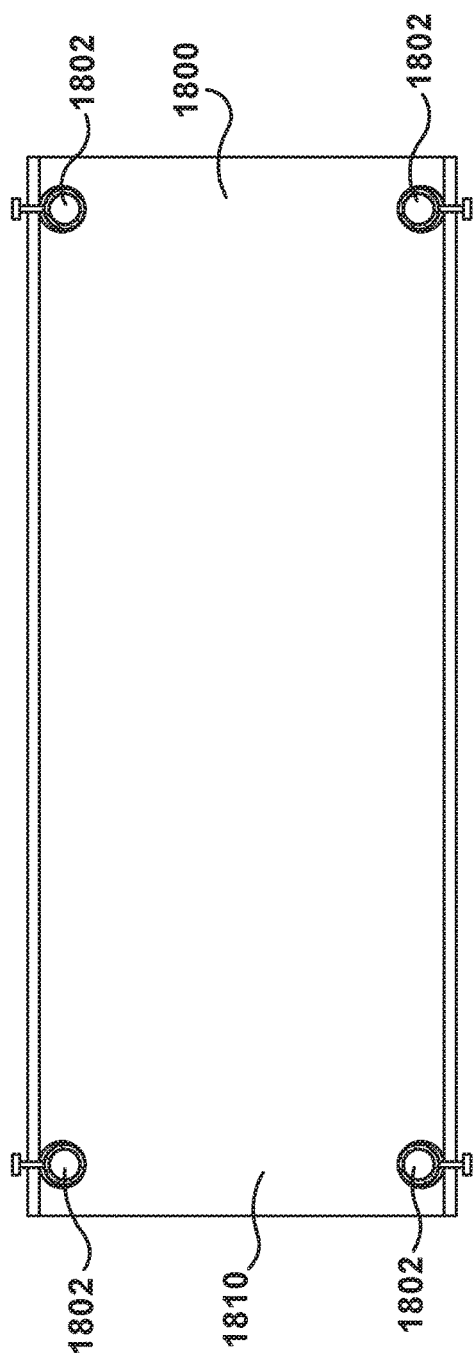
FIG. 19A is a top view of a support table formable from the packaging.
Figure 19C:
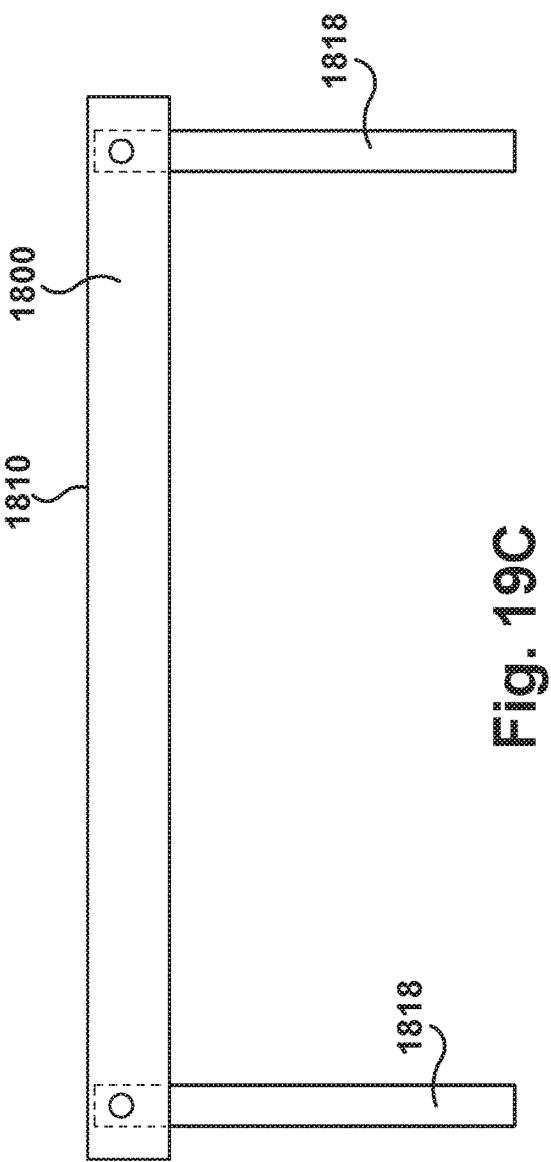
FIG. 19C is a side view of a support table formable from the packaging.

FIGS. 19A-19C illustrate another example embodiment of a table 1800 that can be used with a medical device or a support therefor, including the stabilizing unit 106 of FIG. 1A-6 or the stabilizing unit 200 of FIG. 12. The table 1800 has an elongate surface 1810, and a plurality of support members, or legs, 1818. In certain embodiments, the legs 1818 are tubes. The legs are connected to the table with set screws 1802. The tubes can be moved into openings in the tray during shipping and later connected to the table with set screws. FIG. 19B is a close-up view of the set screws in FIG. 19a. If desired, the table can include lateral sides and can incorporate a lip (not shown), which can be analogous to the lip 114 of the table 108 of FIG. 6. Although the elongate surface is shown as a unitary, contiguous surface, the elongate surface, may be constructed from multiple pieces which can be secured together. For instance, the elongate surface 1810 can be formed from two, or more, hingeably coupled pieces, or multiple pieces can be joined in a snap-fit fashion.

General Considerations

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and subcombinations with one another. The methods, devices, and systems are not limited to any specific aspect or feature or combination thereof, nor do the disclosed embodiments require that any one or more specific advantages be present or problems be solved.

Features and characteristics described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. All combinations or subcombinations of features of the foregoing exemplary embodiments are contemplated by this application, e.g., features of one embodiment can be incorporated into other embodiments. The scope of the invention is defined by the following claims. We therefore claim as our invention all that comes within the scope and spirit of these claims.

What is claimed is:

1. A stabilizing apparatus for a medical device, comprising:
    a housing having an aperture to receive the medical device;
    an engagement member disposed in the housing; and
    a biasing element that urges the engagement member against a surface of the medical device, when the medical device is placed in the housing,
    wherein the stabilizing apparatus clamps and fixes a position of the medical device relative to the housing by releasing the engagement member.

2. The stabilizing apparatus of claim 1 wherein the aperture is positioned at an upper portion of the housing.

3. The stabilizing apparatus of claim 1 wherein the aperture is positioned at a lower portion of the housing.

4. The stabilizing apparatus of claim 1 wherein the aperture is positioned at a side portion of the housing.

5. The stabilizing apparatus of claim 1 further comprising a door connected to the housing, wherein the door has a first position and a second position, wherein the door covers the aperture and engages the housing when the door is in the second position.

6. The stabilizing apparatus of claim 5, wherein the door is slideably adjustable from the first position to the second position.

7. The stabilizing apparatus of claim 5, wherein the door is pivotally adjustable from the first position to the second position.

8. The stabilizing apparatus of claim 1 wherein the biasing element is positioned below the medical device.

9. The stabilizing apparatus of claim 1 wherein the biasing element is positioned above the medical device.

10. The stabilizing apparatus of claim 1, wherein the biasing element is positioned to one side of the medical device.

11. The stabilizing apparatus of claim 1 wherein the housing is adjustable in height.

12. The stabilizing apparatus of claim 1 wherein the biasing element comprises a spring.

13. A stabilizing apparatus for a medical device, comprising:
    a housing having an aperture to receive the medical device;
    an engagement member disposed in the housing; and
    a spring that urges the engagement member against a surface of the medical device when the medical device is placed in the housing,
    wherein the stabilizing apparatus clamps and fixes a position of the medical device relative to the housing by releasing the engagement member.

14. A stabilizing apparatus for a medical device, comprising:
    a housing having an aperture to receive the medical device;
    an engagement member disposed in the housing; and
    a spring positioned below the medical device, wherein the spring urges the engagement member against a surface of the medical device, when the medical device is placed in the housing,
    wherein the stabilizing apparatus clamps and fixes a position of the medical device relative to the housing by releasing the engagement member.

* * * * *